US009150619B2

(12) United States Patent
Edwards et al.

(10) Patent No.: US 9,150,619 B2

(45) Date of Patent: Oct. 6, 2015

(54) METHOD OF ELICTING OR INDUCING AN IMMUNE RESPONSE

(75) Inventors: Stirling John Edwards, Pascoe Vale South (AU); Martin John Pearse, Parkdale (AU); Jean-Pierre Yves Scheerlinck, Mount Waverly (AU); Philip Sutton, Keilor Downs (AU)

(73) Assignees: CSL Limited, Victoria (AU); The University of Melbourne, Victoria (AU)

( * ) Notice: Subject to any disclaimer, the term of this patent is extended or adjusted under 35 U.S.C. 154(b) by 0 days.

(21) Appl. No.: 12/439,054

(22) PCT Filed: Aug. 31, 2007

(86) PCT No.: PCT/AU2007/001277

§ 371 (c)(1),
(2), (4) Date: Jul. 29, 2009

(87) PCT Pub. No.: WO2008/025095

PCT Pub. Date: Mar. 6, 2008

(65) Prior Publication Data

US 2009/0324642 A1 Dec. 31, 2009

(30) Foreign Application Priority Data

Sep. 1, 2006 (AU) ................................ 2006904796

(51) Int. Cl.

| | |
|---|---|
| ***A61K 39/395*** | (2006.01) |
| ***C07K 14/005*** | (2006.01) |
| ***A61K 39/145*** | (2006.01) |
| *A61K 39/00* | (2006.01) |

(52) U.S. Cl.

CPC ............ *C07K 14/005* (2013.01); *A61K 39/145* (2013.01); *A61K 2039/5252* (2013.01); *A61K 2039/54* (2013.01); *A61K 2039/544* (2013.01); *A61K 2039/545* (2013.01); *A61K 2039/55555* (2013.01); *A61K 2039/55561* (2013.01); *A61K 2039/55566* (2013.01); *A61K 2039/55572* (2013.01); *A61K 2039/55577* (2013.01); *C12N 2710/16122* (2013.01); *C12N 2710/16134* (2013.01); *C12N 2760/16122* (2013.01); *C12N 2760/16134* (2013.01)

(58) Field of Classification Search

None

See application file for complete search history.

(56) References Cited

U.S. PATENT DOCUMENTS

| | | | | |
|---|---|---|---|---|
| 6,518,239 | B1 | 2/2003 | Kuo et al. | |
| 2002/0031543 | A1 * | 3/2002 | Iwaarden et al. | ............ 424/450 |
| 2003/0190333 | A1 | 10/2003 | Mossman et al. | |

FOREIGN PATENT DOCUMENTS

| | | | | |
|---|---|---|---|---|
| GB | WO 95/17209 | | * | 12/1994 |
| WO | WO 99/52547 | A1 | | 10/1999 |
| WO | WO 01/75096 | A1 | | 10/2001 |
| WO | WO 01/95934 | A2 | | 12/2001 |
| WO | WO 02/20045 | A2 | | 3/2002 |
| WO | WO 2005/070415 | A1 | | 8/2005 |
| WO | WO 2005/110379 | A2 | | 11/2005 |

OTHER PUBLICATIONS

International Search Report issued on Nov. 2, 2007 in application No. PCT/AU2007/001277.

U.S. Appl. No. 12/679,654, filed Oct. 9, 2008, Pearse et al.

Alpar et al., "Biodegradable mucoadhesive particulates for nasal and pulmonary antigen and DNA delivery," *Advanced Drug Delivery Reviews*, vol. 57, pp. 411-430, 2005.

Bennett et al., "Aerosolized measles and measles-rubella vaccines induce better measles antibody booster responses than injected vaccines: randomized trials in Mexican schoolchildren," *Bulletin of World Health Organization*, vol. 80, No. 10, pp. 806-812, 2002.

Bivas-Benita et al., "Non-invasive pulmonary aerosol delivery in mice by the endotracheal route," *European Journal of Pharmaceutics and Biopharmaceutics*, vol. 61, pp. 214-218, 2005.

Eyles et al., "Analysis of local and systemic immunological responses after intra-tracheal, intra-nasal and intra-muscular administration of microsphere co-encapsulated *Yersinia pestis* sub-unit vaccines,"*Vaccine*, vol. 16, No. 20, pp. 2000-2009, 1998.

Fujihashi et al., "A dilemma for mucosal vaccination: efficacy versus toxicity using enterotoxin-based adjuvants," *Vaccine*, vol. 20, pp. 2431-2438, 2002.

Griffiths et al., "Liposomally-encapsulated ricin toxoid vaccine delivered intratracheally elicits a good immune response and protects against a lethal pulmonary dose of ricin toxin," *Vaccine*, vol. 17/18, pp. 1933-1939, 1997.

Hogenesch et al.., "Systemic and pulmonary immune response to intrabronchial administration of ovalbumin in calves," *Veterinary Immunology and Immunopathology*, vol. 51, pp. 293-302, 1996.

Honko et al., "Flagellin is an Effective Adjuvant for Immunization against Lethal Respiratory Challenge with *Yersinia pestis*," *Infection and Immunity*, vol. 74, No. 2, pp. 1113-1120, Feb. 2006.

Hu et al., "The immunostimulating complex (ISCOM) is an efficient mucosal delivery system for respiratory syncytial virus (RSV) envelope antigens," *Clin. Exp. Immunol.*, vol. 113, pp. 235-243, 1998.

Lombry et al., "Local and Systemic Immune Responses to Intratracheal Instillation of Antigen and DNA Vaccines in Mice," *Pharmaceutical Research*, vol. 21, No. 1, pp. 127-135, Jan. 2004.

Lu et al., "Pulmonary vaccine delivery," *Expert Rev. Vaccines*, vol. 6, No. 2, pp. 213-226, 2007.

(Continued)

*Primary Examiner* — Yunsoo Kim

(74) *Attorney, Agent, or Firm* — Foley & Lardner LLP

(57) ABSTRACT

A method for eliciting or inducing an immune response in a human or animal subject, comprises administering to said subject a composition comprising an antigen and an adjuvant, wherein the composition is administered to the subject by the intra-lung route.

19 Claims, 14 Drawing Sheets

(56) References Cited

OTHER PUBLICATIONS

Lu et al., "Liposomal Dry Powders as Aerosols for Pulmonary Delivery of Proteins," *AAPS PharmSciTech*, vol. 6, No. 4, pp. E641-E648, 2005.
Maloy et al., "Induction of Th1 and Th2 CD4+ T cell responses by oral or parenteral immunization with ISCOMS," *Eur. J. Immunol.*, vol. 25, pp. 2835-2841, 1995.
McBride et al., "Systemic and pulmonary antibody responses of calves to *Pasteurella haemolytica* after intrapulmonary inoculation," *Am. J. Vet. Res.*, vol. 53, No. 10, pp. 1889-1894, Oct. 1992.
Menzel et al., "Inhalative vaccination with pneumococcal polysaccharide in healthy volunteers," *Vaccine*, vol. 23, pp. 5113-5119, 2005.
Meyer et al., "Inhalative vaccination with pneumococcal polysaccharide in patients with chronic obstructive pulmonary disease," *Vaccine*, vol. 24, pp. 5832-5838, 2006.
Nardelli-Haefliger et al., "Immune responses induced by lower airway mucosal immunization with a human papillomaviurs type 16 virus-like particle vaccine," *Vaccine*, vol. 23, pp. 3634-3641, 2005.
Nesburn et al., "Local and systemic B cell and Th1 responses induced following ocular mucosal delivery of multiple epitopes of herpes simplex virus type 1 glycoprotein D together with cytosine-phosphate-guanine adjuvant," *Vaccine*, vol. 23, pp. 873-883, 2005.
Orson et al., "Protection against influenza infection by cytokine-enhanced aerosol genetic immunization," *The Journal of Gene Medicine*, vol. 8, pp. 488-497, 2006.
Pabst et al., "A Single Intratracheal Dose of the Growth Factor Fms-Like Tyrosine Kinase Receptor-3 Ligand Induces a Rapid Differential Increase of Dendritic Cells and Lympocyte Subsets in Lung tissue and Bronchoalveolar Lavage, Resulting in an Increased Local Antibody Production," *The Journal of Immunology*,vol. 171, pp. 325-330, 2003.
Smith et al., "Evaluation of novel aerosol formulations designed for mucosal vaccination against influenza virus," *Vaccine*, vol. 21, pp. 2805-2812, 2003.
Stanley et al., "Intranasal immunisation with *Toxoplasma gondii* tachyzoite antigen encapsulated into PLG microspheres induces humoral and cell-mediated immunity in sheep," *Vaccine*, vol. 22, pp. 3929-3941, 2004.
Waldman et al., "An Evaluation of Influenza Immunization," *Bull. Wdl. Hlth. Org.*, vol. 41, pp. 543-548, 1969.
Wigley et al., "Aerosol Immunization of Human with Tetnaus Toxoid," *The Journal of Immunology*, vol. 103, No. 5, pp. 1096-1098, Nov. 1969.
Zanvit et al., "Immune response after adjuvant mucosal immunization of mice with inactivated influenza virus," *Immunology Letters*, vol. 97, pp. 251-259, 2005.
International Search Report issued on Dec. 16, 2008 in application No. PCT/AU2008/001500 (corresponding to U.S. Appl. No. 12/679,654).
Ennis et al., "Augmentation of Human Influenza A Virus-Specific Cytotoxic T Lymphocyte Memory by Influenza Vaccine and Adjuvanted Carriers (ISCOMS)," *Virology*, vol. 259, pp. 256-261, 1999.
Coulter et al., "Intranasal vaccination with ISCOMATRIX® adjuvanted influenza vaccine," *Vaccine*, vol. 21, pp. 946-949, 2003.
Windon et al., "Local immune responses to influenza antigen are synergistically enhanced by the adjuvant ISCOMATRIX®," *Vaccine*, vol. 20, pp. 490-497, 2001.
Scheerlinck et al., "Local immune responses following nasal delivery of an adjuvanted influenza vaccine," *Vaccine*, vol. 24, pp. 3929-3936, 2006.
Sambhara et al., "Heterosubtypic Immunity against Human Influenza A Viruses, Including Recently Emerged Avian H5 and H9 Viruses, Induced by FLU-ISCOMM Vaccine in Mice Requires both Cytotoxic T-Lymphocyte and Macrophage Function," *Cellular Immunology*, vol. 211, pp. 143-153, 2001.
Pearse et al., "ISCOMATRIX® adjuvant for antigen delivery," Advanced Drug Delivery Reviews, vol. 57, pp. 465-474, 2005.
De Haan et al., "Induction of a secretory IgA response in the murine female urogenital tract by immunization of the lungs with liposome-supplemented viral subunit antigen," Vaccine, vol. 13, No. 7, pp. 613-616, 1995.
Marshall et al., "Antibodies to the Major Linear Neutralizing Domains of Cytomegalovirus Glycoprotein B Among Natural Seropositives and CMV Vaccine Recipients," Viral Immunology, vol. 13, No. 3, pp. 329-341, 2000.
Sjölander et al., "Intranasal immunisation with influenza-ISCOM induces strong mucosal as well as systemic antibody and cytotoxic T-lymphocyte responses," Vaccine, vol. 19, pp. 4072-4080, 2001.
Rimmelzwaan et al., "A single dose of an ISCOM influenza vaccine induces long-lasting protective immunity against homologous challenge infection but fails to protect *Cynomolgus macaques* against drift variants of influenza A (H3N2) viruses," Vaccine, vol. 20, pp. 158-163, 2002.
Notice of Allowance issued on Nov. 26, 2014 in U.S. Appl. No. 12/679,654 (US 2010/0291146).

* cited by examiner

IMX = ISCOMATRIX™ adjuvant

IMX = ISCOMATRIX™ adjuvant

IMX = ISCOMATRIX$^{TM}$ adjuvant

IMX = ISCOMATRIX™ adjuvant

*Significantly greater than upper lung vaccination; $p<0.05$

— = mean
* In comparison with preimmunisation (preimmune) sera
No significant difference between intra-lung (Lung) and subcutaneous (S/C) groups

* Sig different from "No adjuvant" ($p<0.05$)

* Sig different from "No adjuvant" ($p<0.032$)

IMX = ISCOMATRIX™ adjuvant

* Sig different from "No adjuvant" ($p<0.008$)

* Sig different from "No adjuvant" ($p<0.05$)

IMX = ISCOMATRIX™ adjuvant

10a

* Sig different from "No adjuvant" (p<0.02)

10b

* Sig different from "No adjuvant" (p<0.04)

IMX = ISCOMATRIX™ adjuvant

METHOD OF ELICTING OR INDUCING AN IMMUNE RESPONSE

FIELD OF THE INVENTION

This invention relates to a method of eliciting or inducing an immune response in a subject, particularly a human subject, and more particularly to a method which utilises a needle-less route of administration, thereby providing an alternative to the more traditional injection routes for administration of vaccines such as the subcutaneous and intramuscular routes.

BACKGROUND OF THE INVENTION

Over many years, various attempts have been made to utilise the respiratory tract as a means to deliver non-living vaccine antigens. This route was seen as conferring advantages in terms of vaccine acceptability (avoiding "needle phobia"), the opportunity to induce local immune responses and the potential to induce responses at distant mucosal sites given the assumed unity of the mucosal immune system. Much attention has been given to delivering vaccines by the intranasal route in humans and animals. Results to date indicate that this route requires very high antigen doses and/or the use of specialised delivery technologies to ensure antigen uptake and immune induction.

Similarly, delivery of vaccines via the intra-lung or pulmonary route has in the past generally required specialised delivery techniques, such as microencapsulation (see, for example, Oya Alpa et al., 2005), in order to optimise immune responses.

In work leading to the present invention, the inventors have observed that delivery of vaccines by the intranasal route is highly inefficient, inducing poor local immunity even at high antigen doses. Accordingly, the inventors have investigated an alternative route of vaccine administration which retains the advantage of avoiding "needle phobia".

Surprisingly, the inventors have demonstrated the superiority of vaccine delivery to the lung over that by the intranasal route as a means of inducing immune responses. They have also demonstrated that strong systemic immune responses can be induced using very small quantities of antigen when delivered with adjuvant via the lung. In particular, the inventors have shown that a straightforward vaccine composition combining antigen and adjuvant induces strong systemic immune responses on intra-lung delivery without the need for specialised uptake technologies. Significantly, it has been shown that intra-lung delivery results in lung mucosal immune responses, which can be as much as one hundred-fold (100×) greater than that induced by conventional parenteral immunisation, even when very small quantities of antigen are delivered with adjuvant via the lung.

Griffith et al (1997) describe the intratracheal delivery of ricin toxoid formulated either in liposomes, with aluminium hydroxide or in PBS. The liposome formulated group showed best protection; aluminium hydroxide did not improve protection over PBS. WO 2005/110379 describes the pulmonary delivery of a particulate malaria vaccine. The formulation was delivered as a particulate formulation and permitted sustained release of antigen.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Throughout this specification and the claims which follow, unless the context requires otherwise, the word "comprise", and or variations such as "comprises" or "comprising", will be understood to imply the inclusion of a stated integer or step or group of integers or steps but not the exclusion of any other integer or step or group of integers or steps.

SUMMARY OF THE INVENTION

The present invention provides a method for eliciting or inducing an immune response in a human or animal subject, which comprises administering to said subject a composition comprising an antigen and an adjuvant, wherein the composition is administered to the subject by the intra-lung or pulmonary route.

Preferably, the composition is formulated to be suitable for intra-lung or pulmonary administration.

In another aspect, the present invention provides the use of a composition comprising an antigen and an adjuvant in, or in the manufacture of a medicament for, intra-lung or pulmonary administration to a human or animal subject to elicit or induce an immune response in the subject.

In yet another aspect, the invention provides an agent for eliciting or inducing an immune response in a human or animal subject by the intra-lung or pulmonary route, wherein said agent is a composition comprising an antigen and an adjuvant.

Horizontal bar=median value

Open bar=middle 50% of values

Vertical line=10 and 90 percentiles.

Figure 1:
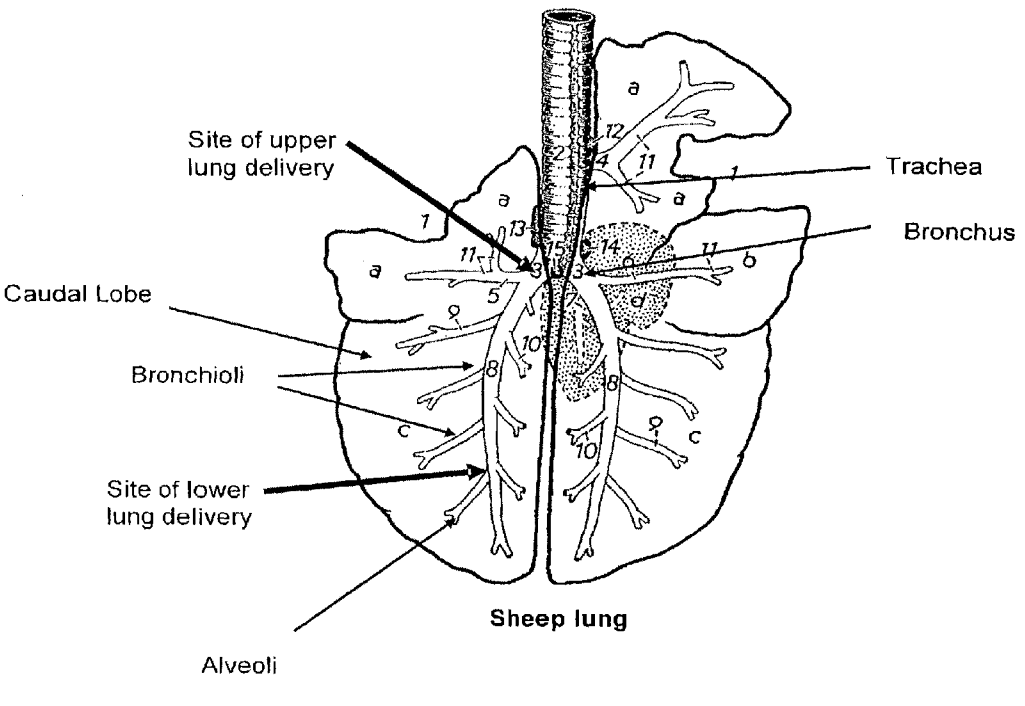
Figure 2A:
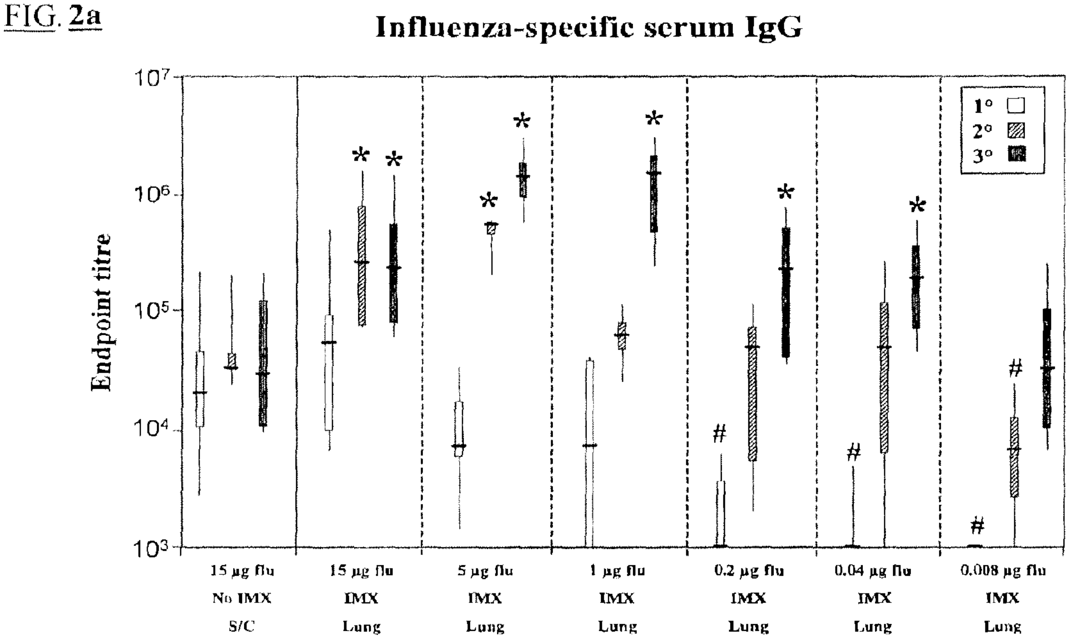
In FIGS. 2, 3, 4, 6, 9 and 10.
Figure 2B:
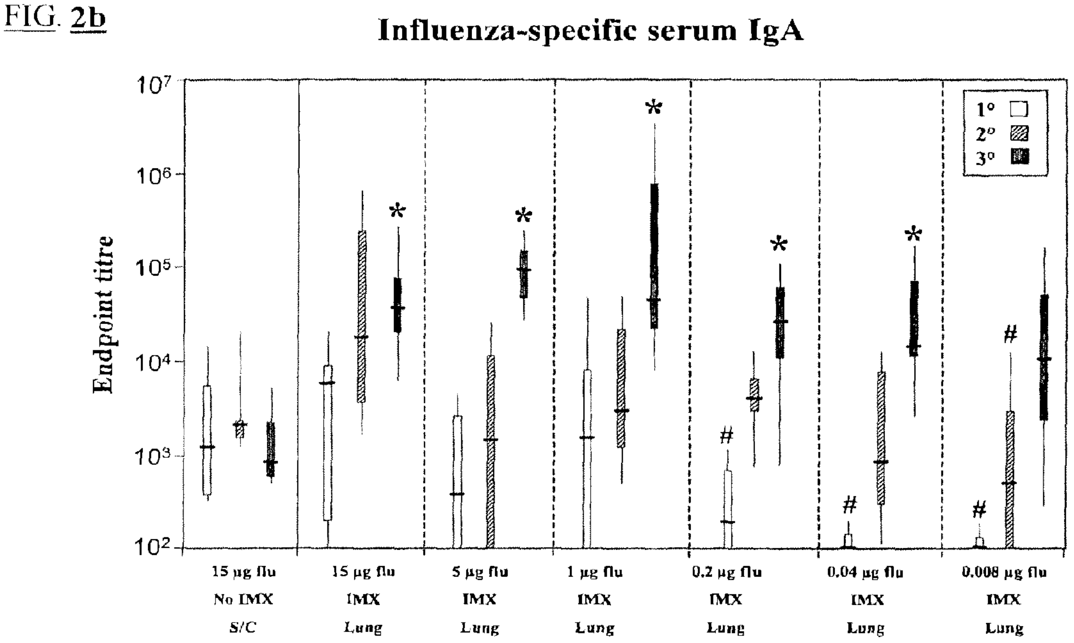
Figure 2C:
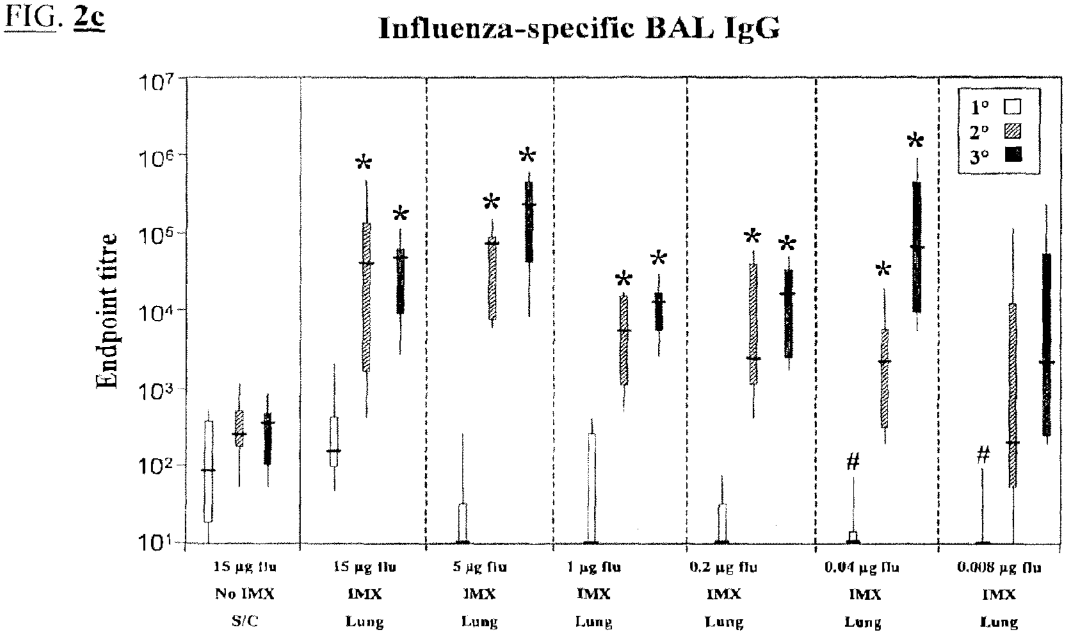
Figure 2D:
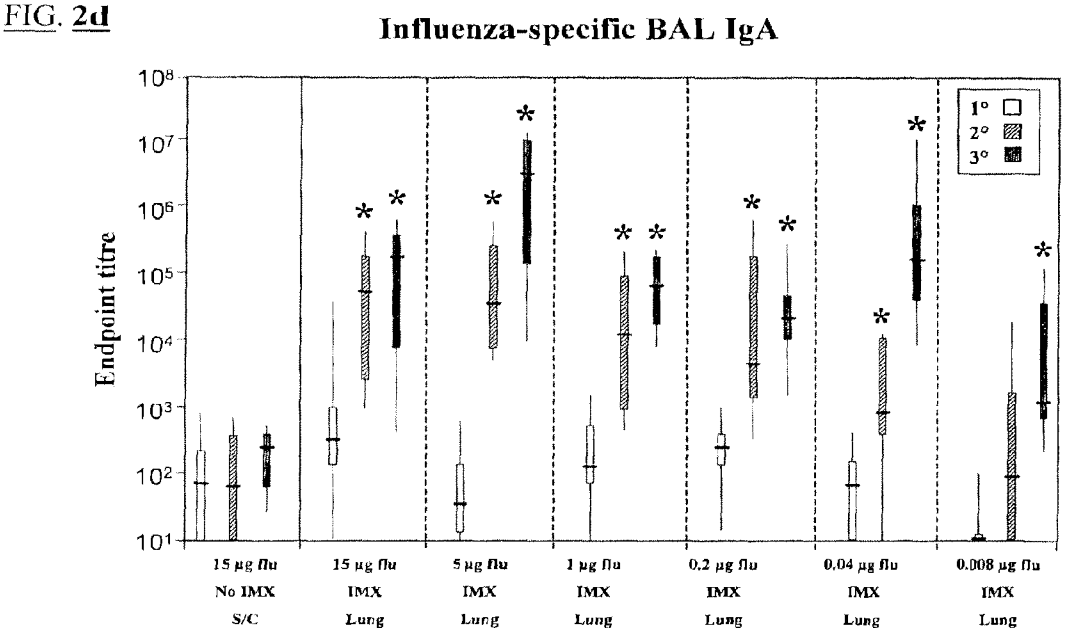
Figure 3A:
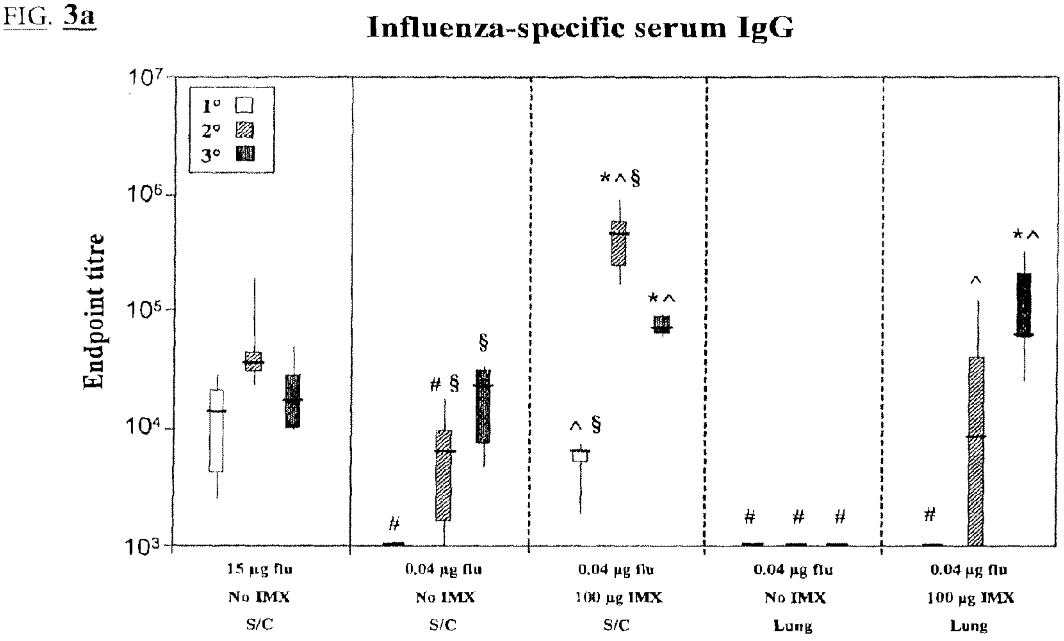
Figure 3B:
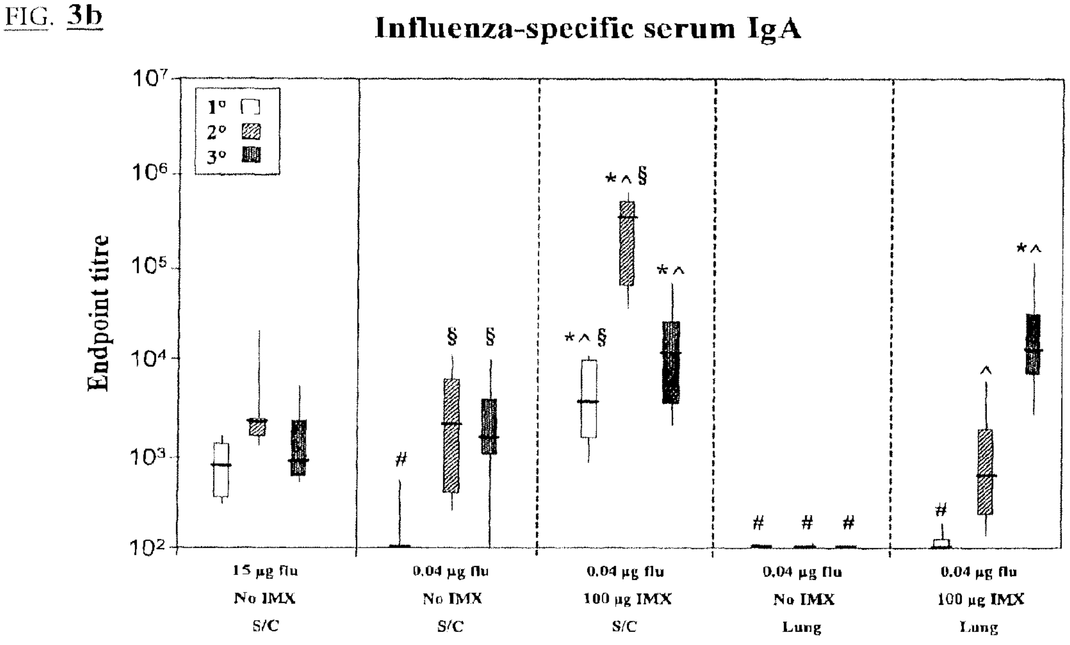
Figure 3C:
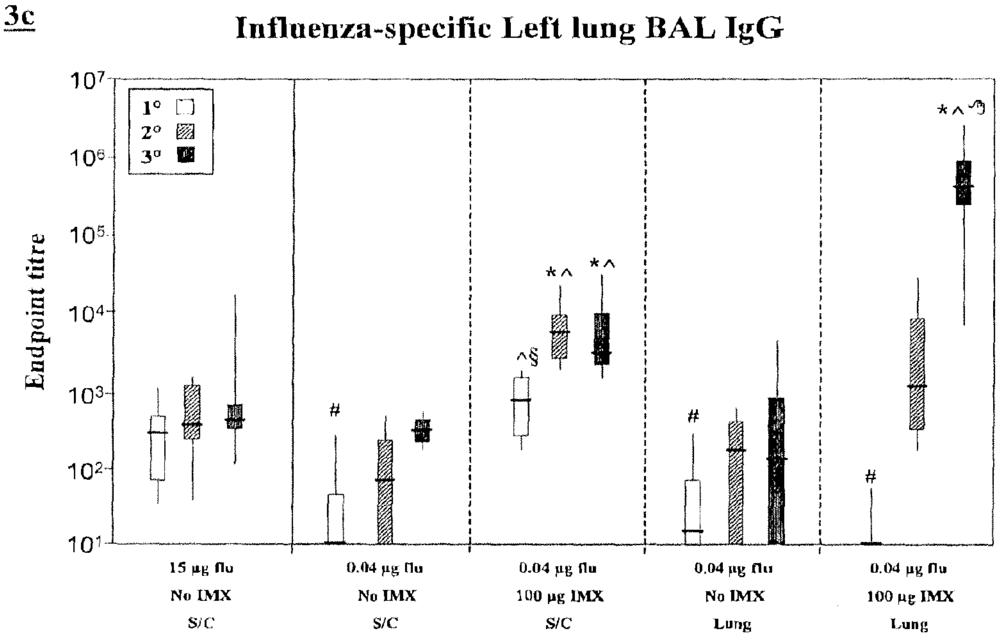
Figure 3D:
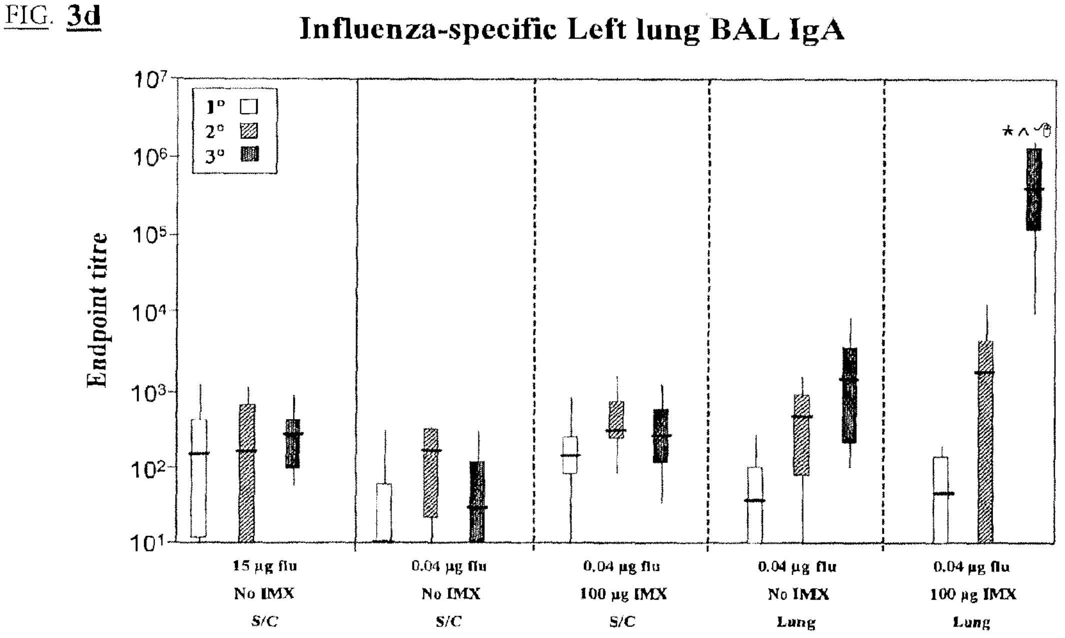

FIG. 1 is a diagram of the sheep lung illustrating the regions which correspond to upper lung and lower (or deep) lung (lung diagram modified from Nickel et al., 1979).

FIGS. 2 and 3 are graphical representations of the results obtained in initial experiments. Groups of sheep were immunised, by the subcutaneous (s/c) or intra-lung (lung) routes with three doses, at three week intervals, of influenza virus antigen (influenza antigen) alone or the antigen formulated with 100 μg ISCOMATRIX™ adjuvant (IMX=ISCOMATRIX™ adjuvant). Blood (serum) and lung (broncho-alveolar lavage—BAL) samples were taken one week prior to the first dose, two weeks after the first and one week following the second and third doses.

FIG. 2 shows antibody responses [influenza-specific end-point titres in an Enzyme Immunoassay (EIA) after one, two and three doses ($1^{0}$, $2^{0}$ and $3^{0}$) of formulations consisting of 15 μg influenza virus antigen alone (equivalent to a monovalent dose of currently available influenza vaccines) and diminishing quantities of influenza antigen formulated with 100 μg ISCOMATRIX™ adjuvant. Assays for both IgG and IgA were carried out on serum and BAL (lung) samples. (* significant differences using Mann-Whitney analysis)

FIG. 3 shows antibody responses using the same immunisation and sampling schedule and assay procedure as for FIG. 2, where immunisation by the subcutaneous and intra-lung routes with a very low dose of influenza antigen (0.04 μg) with and without ISCOMATRIX™ adjuvant was carried out. (#, *, ^, §, 🖰 significant differences using Mann-Whitney analysis)

For FIGS. 4, 6, 7, 9, 10 statistical analysis was carried out after the data was log transformed and the groups compared by analysis of variance (ANOVA) with Dunnett's post-hoc analysis, using SPSS software version 13.

Figure 4:
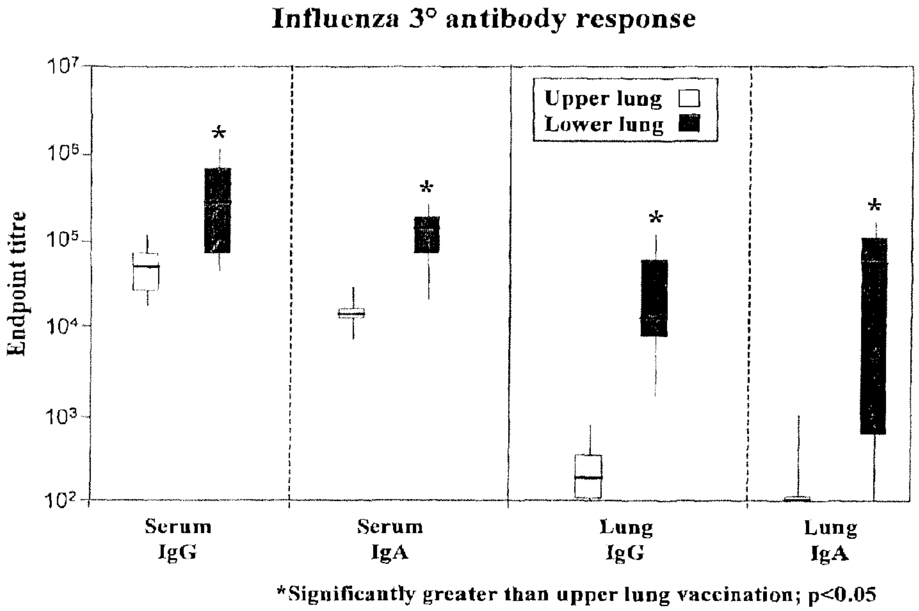

FIG. 4 shows antibody responses in groups of sheep after immunisation with three doses of 0.04 μg influenza antigen formulated with 100 μg ISCOMATRIX™ adjuvant delivered to either the upper or lower lung (FIG. 1). Serum and BAL (lung) samples were collected one week after the third dose.

Figure 5:
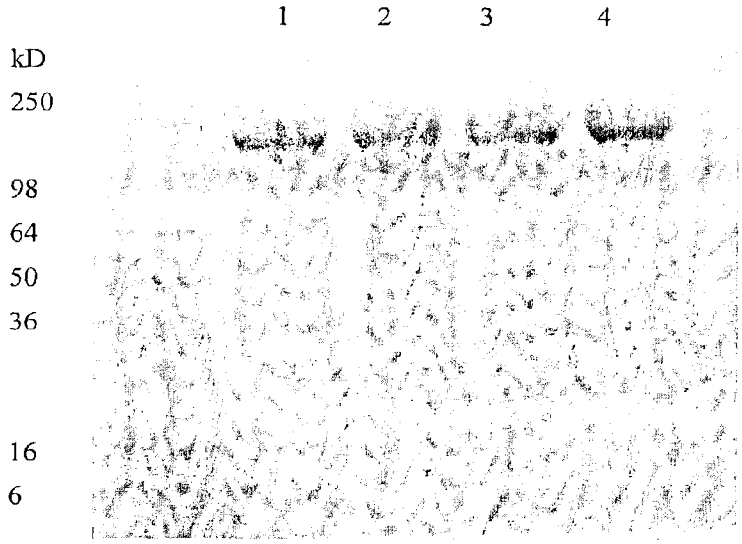

FIG. 5 is a Coomassie-stained SDS Polyacrylamide gel electrophoresis (SDS-PAGE) gel of purified cytomegalovirus (CMV) ΔgB protein, after the protein was purified on an affinity column of the gB-specific 58-15 monoclonal antibody coupled to an NHS-activated HP column. Lanes 1 to 4 show ΔgB purified from four different affinity purification runs.

FIG. 6 shows CMV ΔgB-specific antibody responses in groups of 8 sheep after three doses of CMV ΔgB formulated with 100 μg ISCOMATRIX™ adjuvant delivered by either the subcutaneous or intra-lung routes. Antibody responses in serum and BAL samples were assayed and endpoint titres determined for IgG and IgA using a ΔgB-specific EIA. The graphs show antibody responses two weeks after the first dose (post-primary), and one week after the second (post-secondary) and third (post-tertiary) doses.

(* significant differences using ANOVA).

Figure 6A:
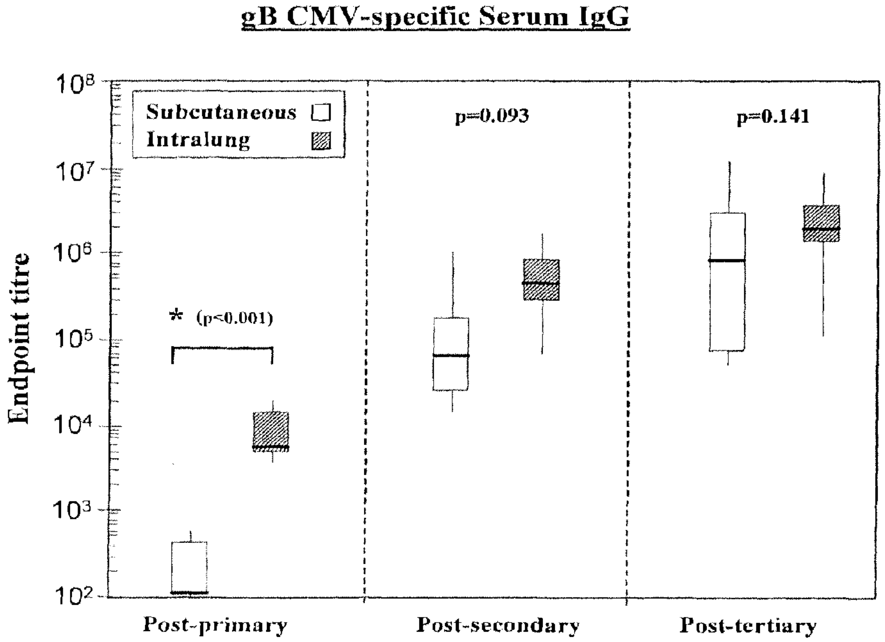
Figure 6B:
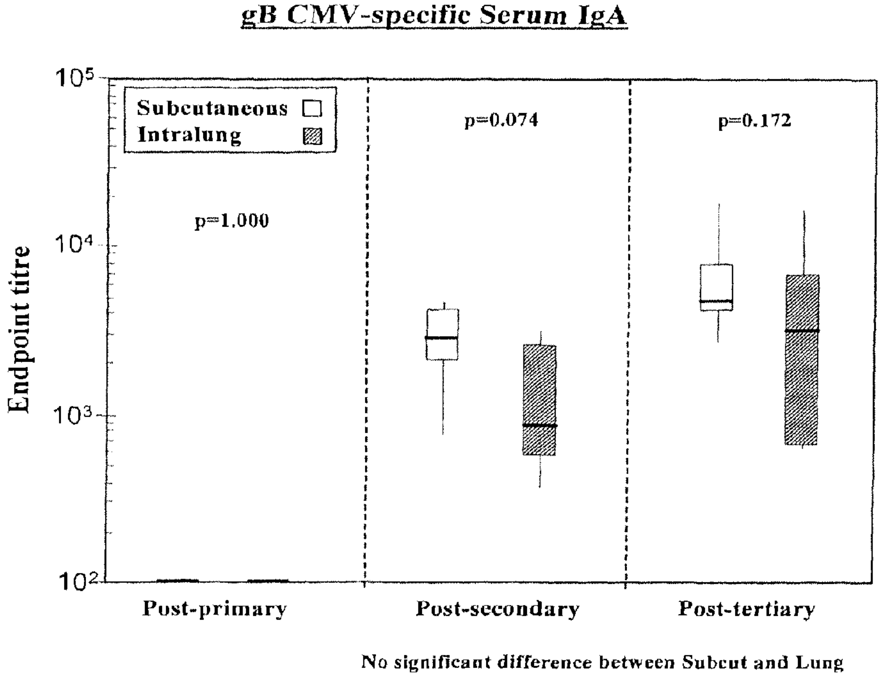
Figure 6C:
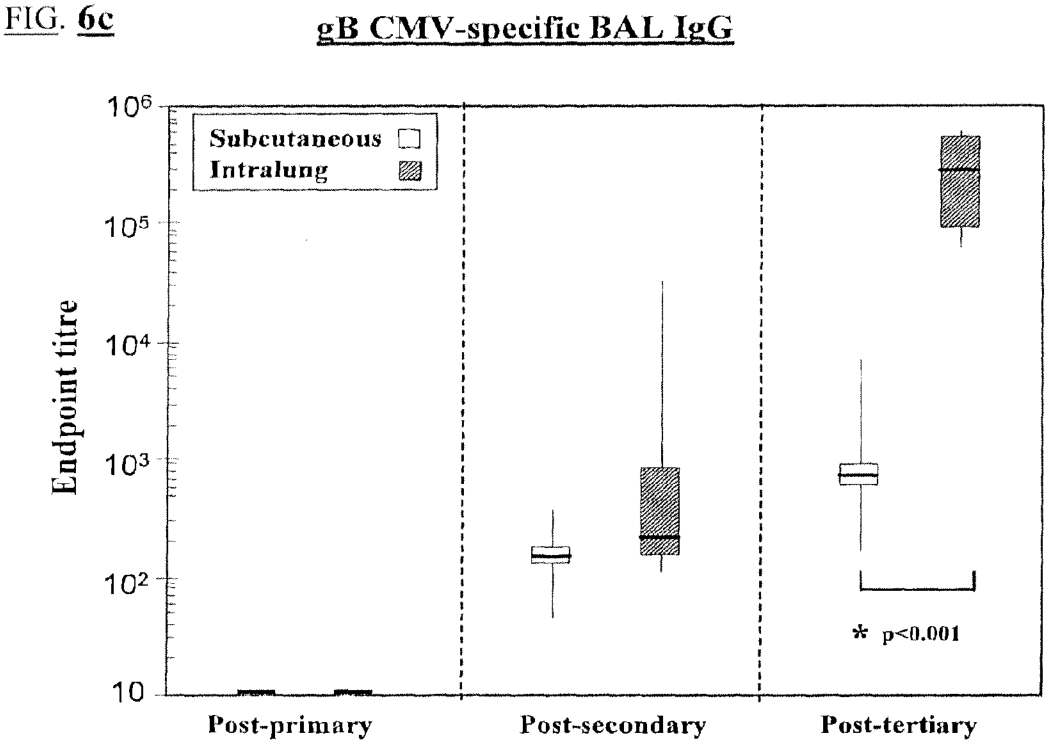
Figure 6D:
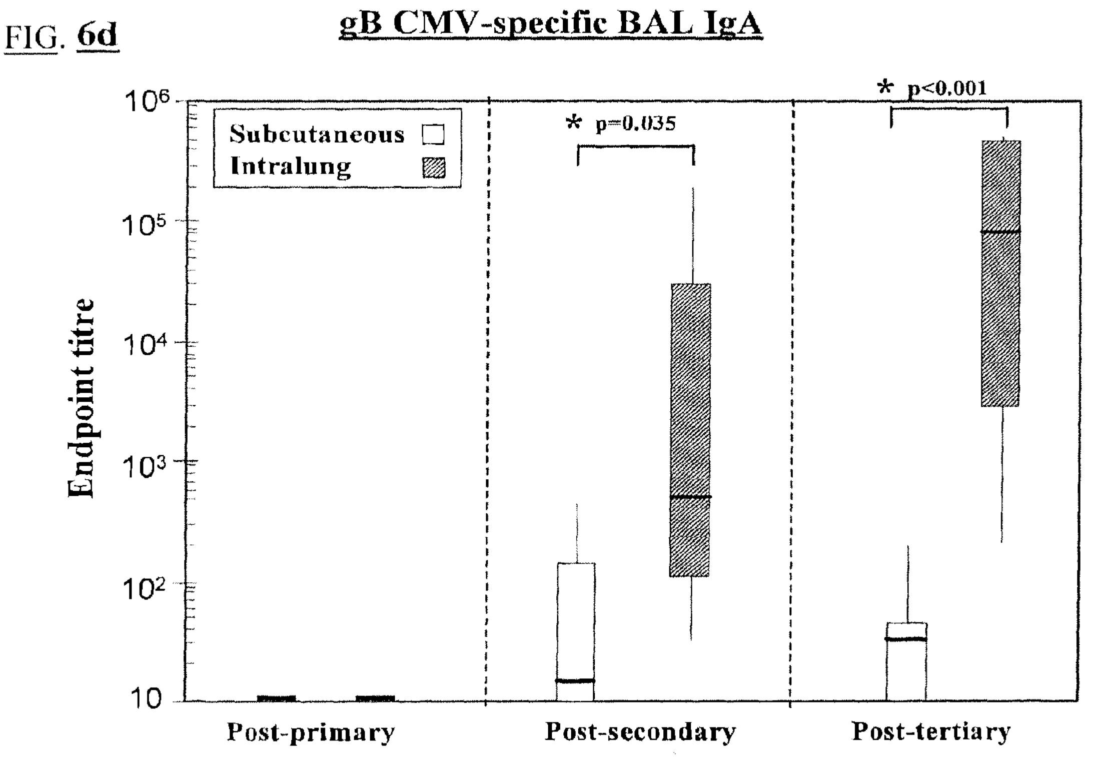
Figure 7:
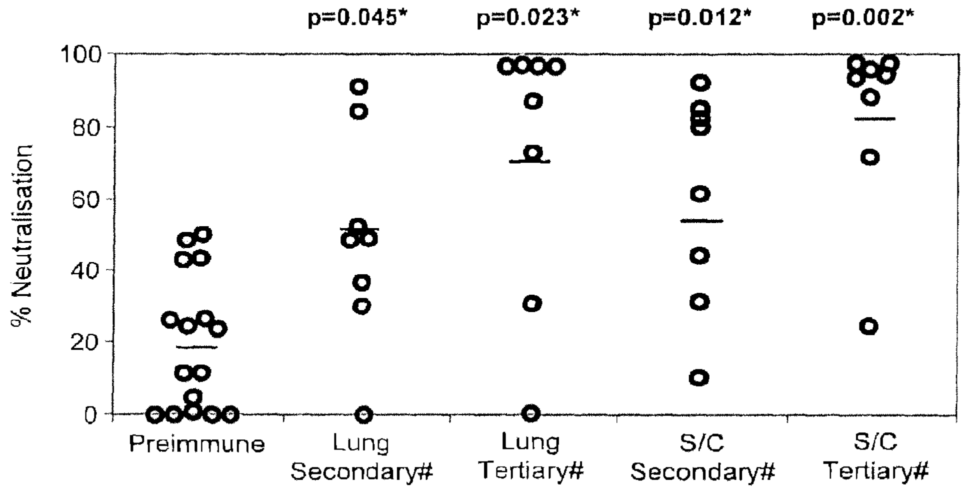

FIG. 7 shows individual percentage neutralisation titres against CMV of individual sheep from the same groups of sheep as FIG. 6. Serum samples from bleeds taken one week prior to the first dose (Preimmune), two weeks after the first dose (Secondary) and one week after the second (Secondary) and third (Tertiary) doses of CMV ΔgB formulated with 100 μg ISCOMATRIX™ adjuvant were assayed for CMV neutralising activity. Each circular point is the percentage neutralisation for an individual sheep serum collected at the nominated dose point. Serum CMV-neutralising titres following two and three doses of the formulation were significantly greater than for preimmune sera for both intra-lung and subcutaneous delivery.

(* significant differences using ANOVA).

Figure 8:
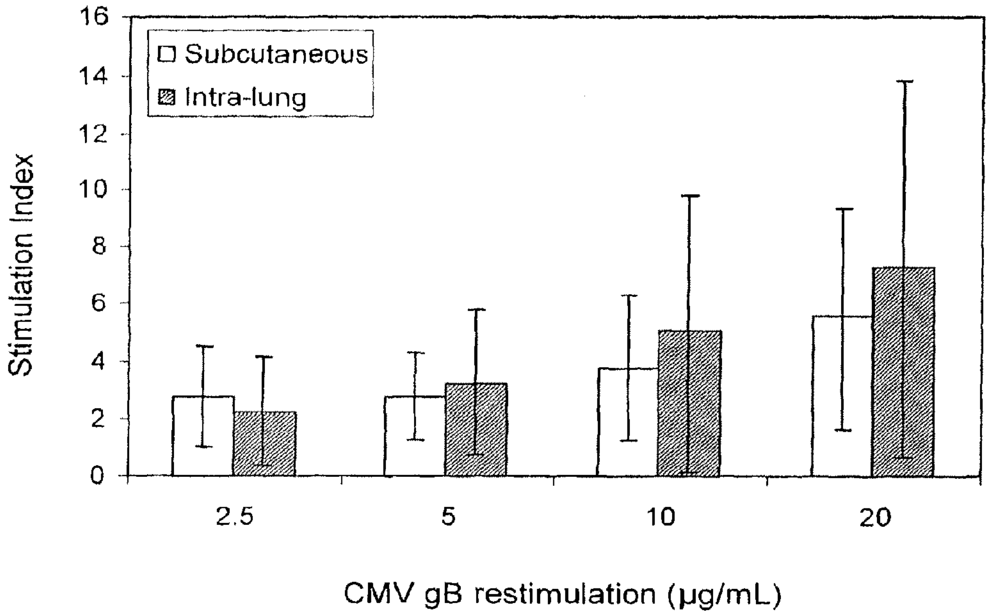
Figure 9A:
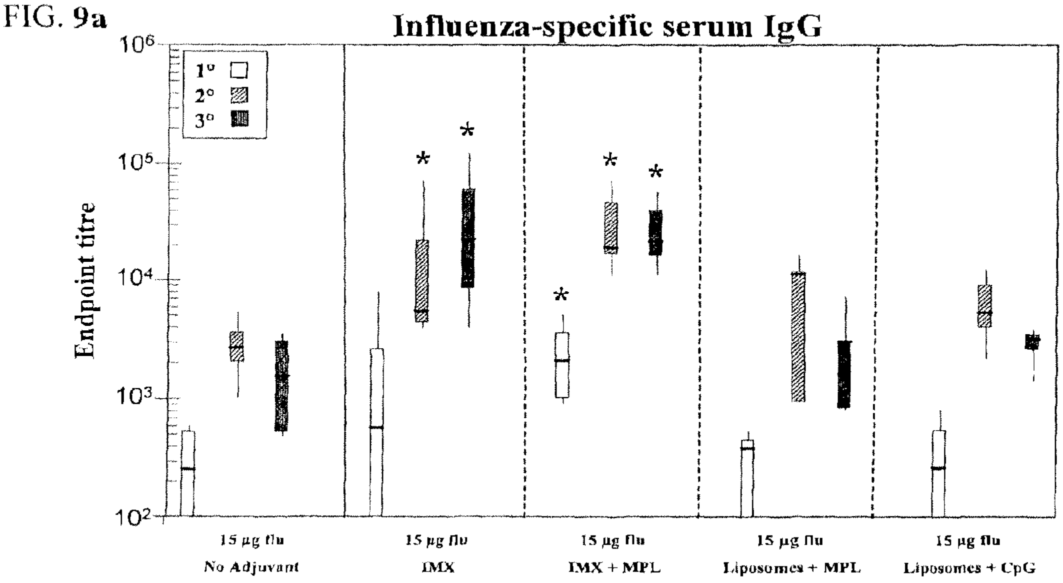
Figure 9B:
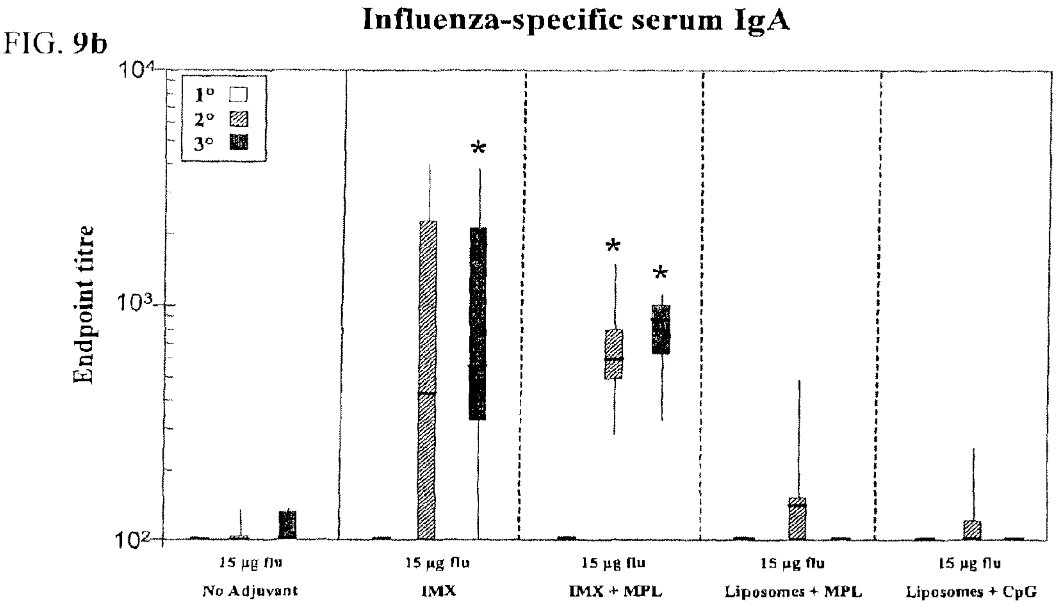
Figure 9C:
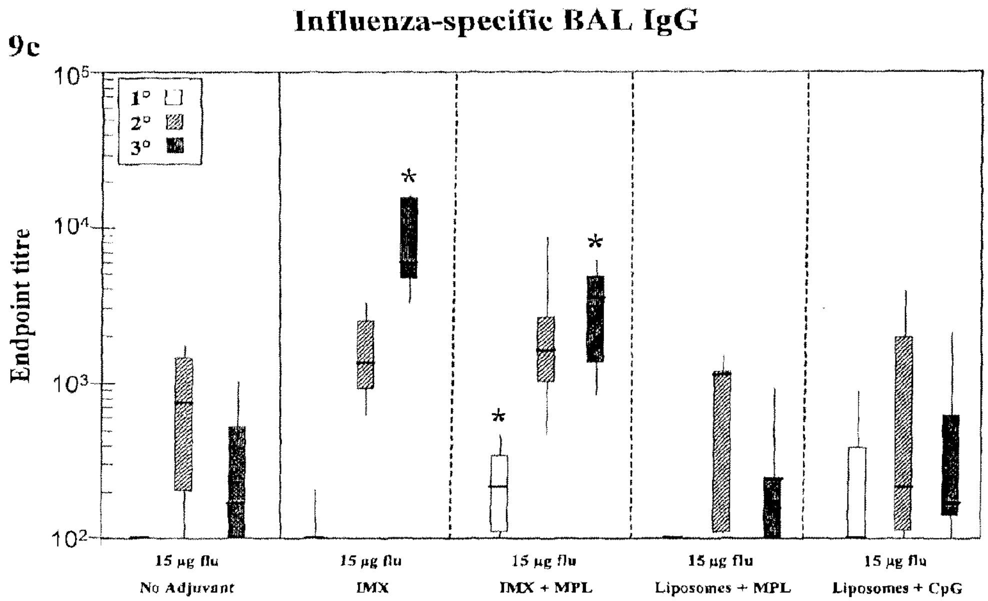
Figure 9D:
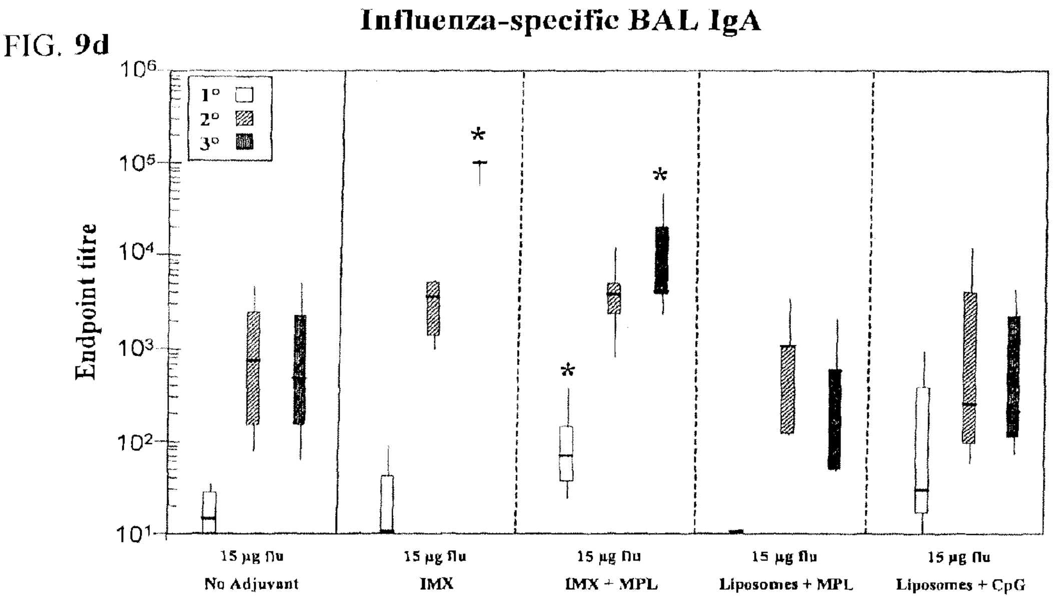

FIG. 8 shows the results of in vitro restimulation of peripheral blood mononuclear cells (PBMCs) following incubation with the ΔgB protein. The PBMCs were collected from the peripheral blood of the same sheep as in Example 7, one week after administration of the third dose of CMV ΔgB formulated with 100 μg ISCOMATRIX™ adjuvant. Following stimulation with ΔgB, cell proliferation was determined by assay of tritiated thymidine incorporated into the cells. Stimulation index (SI) was calculated as the ratio of tritium incorporated into cells stimulated with ΔgB to tritium incorporated into control unstimulated cells. An SI≥4 was considered to be a positive proliferative response.

FIG. 9 shows antibody responses in groups of sheep (4 sheep in Flu No Adjuvant group; 7 sheep in each of adjuvant groups), immunised with influenza antigen formulated with a variety of adjuvants. The immunisation and sampling schedules and assay procedure were the same as for FIG. 1.

(* significant differences using ANOVA).

Figure 10:
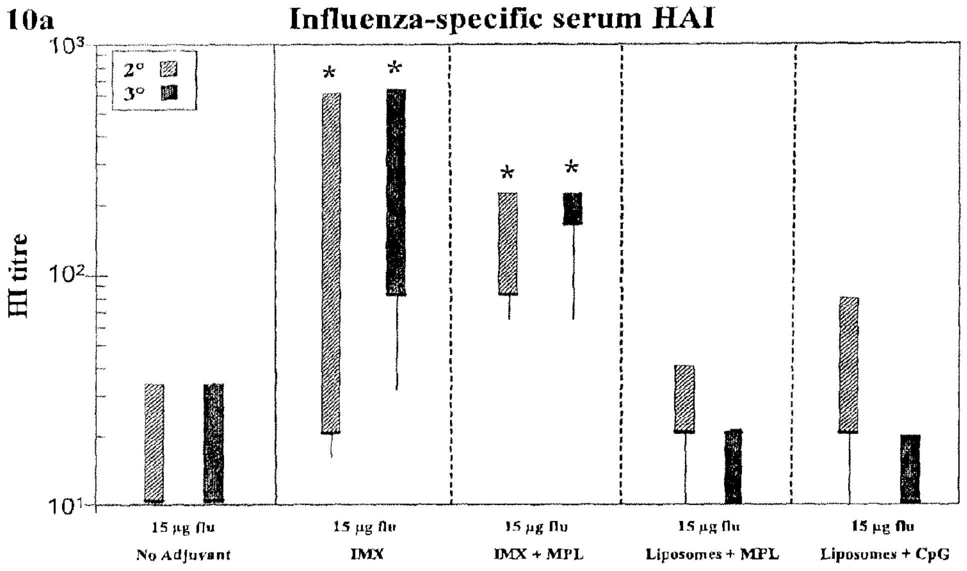
Figure 10:
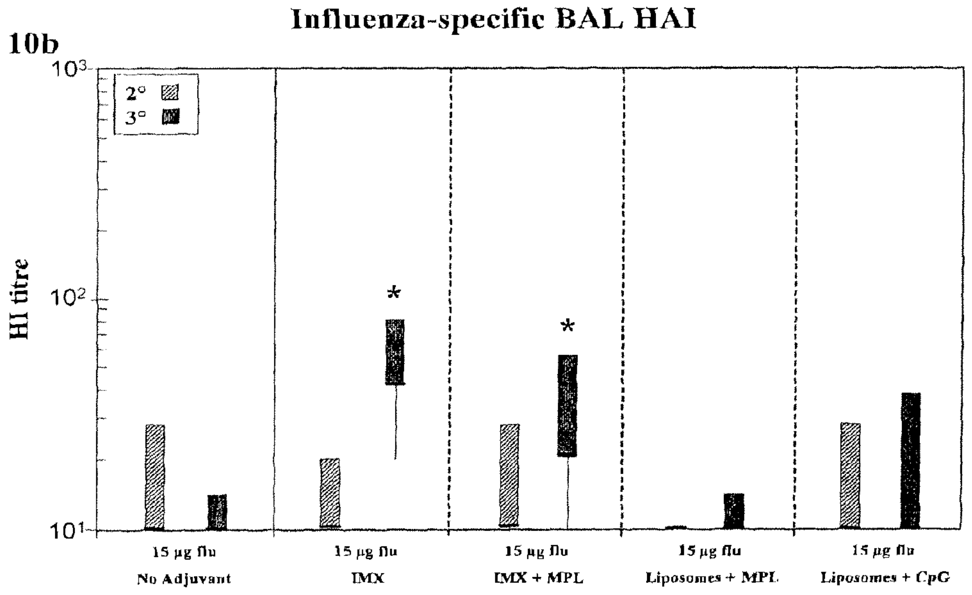

FIG. 10 shows haemagglutination inhibition assay (HAI) results for the same groups of sheep as FIG. 9. HAI titre for each sample was determined by end point inhibition on turkey red cells.

(* significant differences using ANOVA).

DETAILED DESCRIPTION OF THE INVENTION

In one aspect, the present invention provides a method of eliciting or inducing an immune response in a human or animal subject, which comprises administering to said subject a composition comprising an antigen and an adjuvant, wherein the composition is administered to the subject by the intra-lung route.

Preferably, the subject is a human, however the method of the invention also extends to eliciting or inducing an immune response in an animal subject such as a livestock animal (e.g., sheep, cow or horse), laboratory test animal (e.g., mouse, rat, rabbit or guinea pig), companion animal (e.g., dog or cat) or wild animal.

As used herein, references to "intra-lung" or "pulmonary" delivery of a composition refer to delivery of the composition to mucosal surfaces of the lung where the active components of the composition (i.e. antigen and adjuvant) can contact the capillary system in the lung and/or the mucosal immune system. These terms include "deep lung" or "lower lung" delivery of the composition, that is delivery of the composition to the deep bronchi, bronchioli and/or alveoli of the lung.

Preferably, in accordance with this invention the composition comprising antigen and adjuvant is administered into the lung(s) of the subject as an aerosol or in dry powder form, with the aerosol or dry powder being delivered using a nebuliser or similar device. Standard devices or products for intra-lung or pulmonary delivery of pharmaceutically active products are well known to persons skilled in the art.

As indicated above, in another aspect the present invention provides the use of a composition comprising an antigen and an adjuvant in, or in the manufacture of a medicament for, intra-lung administration to a human or animal subject to elicit or induce an immune response in the subject.

In yet another aspect, the invention provides an agent for eliciting or inducing an immune response in a human or animal subject by the intra-lung route, wherein said agent is a composition comprising an antigen and an adjuvant.

Preferably, the antigen which is administered in accordance with the present invention is the antigen which will elicit or induce an immune response against a lung pathogen such as influenza, *Chlamydia pneumoniae*, respiratory syncytial virus, pneumococci, etc. It is to be understood, however, that the antigen may also be selected to elicit or induce an immune response against other pathogens, including pathogens of other mucosal sites, for example, *Helicobacter pylori, Salmonella, E. coli*, cholera, HIV, sexually transmitted disease organisms, etc. Antigen administered in accordance with the present invention has the advantage of high recipient acceptability (avoidance of "needle phobia" and ease of administration). In particular, it results in both strong mucosal and systemic immune responses, indicating that it will be useful for all vaccinations including those reliant upon a systemic immune response.

The antigen may also be a tumour-specific or tumour-associated antigen. Preferably the tumour is one associated with a mucosal site. Tumours associated with mucosal sites include but are not limited to lung tumours, tumours of the gastrointestinal tract and genital tract tumours.

The antigen may be any chemical entity which can elicit or induce an immune response in a human or animal, including but not limited to a whole-cell inactivated bacterium or a subunit thereof, a whole inactivated virus or a subunit thereof, a protein or peptide, a glycoprotein, a carbohydrate, a ganglioside, a polysaccharide, a lipopolysaccharide or a lipopeptide; or it can be a combination of any of these.

Preferably also, the adjuvant is an immunostimulating adjuvant, more preferably a saponin-based adjuvant, and even more particularly an immunostimulating complex (or ISCOM™), such as ISCOMATRIX™ adjuvant. However, the present invention also encompasses the use of other immunostimulating adjuvants, either individually or in combination with another adjuvant such as an immunostimulating complex, including for example liposomes, oil-in-water adjuvants such as MF59, aluminium salt adjuvants such as aluminium hydroxide and aluminium phosphate, lipopolysaccharide adjuvants such as lipid A and monophosphoryl lipid A (MPL), oligonucleotide adjuvants such as CpG oligonucleotide adjuvant, and mucosal adjuvants such as cholera toxin. Suitable immunostimulating adjuvants are described by way of example by Cox and Coulter, 1997.

The composition of the invention may be delivered to the lungs using any one of a number of existing technologies as well as those in development. Numerous examples of mechanical devices able to deliver drug or protein preparations to the lung exist and nebuliser and aerosol devices have been used for decades in the treatment of asthma (see Gonda, 2000). Typically the devices are intended to deliver material to the lungs by oral inhalation. Recent advances in this field (see Edwards and Dunbar, 2002) include those made by the 3M Corporation (Shoyele and Slowey, 2006) and Inhale Therapeutics Systems, Inc. (Kuo and Lechuga-Ballesteros, 2003).

In accordance with this invention, the composition is administered to the human or animal subject in an immunologically effective amount. As used herein, an immunologically effective amount means that amount necessary at least partly to attain the desired immune response, or to delay the onset of, inhibit the progression of, or halt altogether, the onset or progression of the particular condition being treated. This amount varies depending upon the health and physical condition of the individual to be treated, the taxonomic group of individual to be treated, the individual's immune competence, the degree of protection desired, the formulation of the vaccine, the assessment of the medical situation, and other relevant factors. It is expected that the amount will fall in a relatively broad range that can be determined through routine trials.

It is to be noted, however, that particularly important advantages of the present invention include the fact that the intra-lung administration of the vaccine composition comprising an antigen and an adjuvant has been found to give rise not only to a systemic antibody response to the antigen as well as a mucosal response, but also to the possibility of a major reduction in the antigen dose required to elicit or induce such systemic and mucosal responses. In addition, effective intra-lung administration of the vaccine composition in accordance with the present invention avoids the necessity for complex delivery systems such as microencapsulation or mucoadhesive or other technologies to enhance uptake of the vaccine at mucosal sites.

Furthermore, the induction of greatly improved mucosal antibody responses indicates that intra-lung immunisation may enhance vaccine efficacy for mucosal infections and potentially reduce pathogen transmission from an immunised/infected person.

In particular, mucosal antibodies may be of great value in improving protective immunity against influenza challenge. A recent WHO consultation report (Cassetti et al., 2006) stated: "In mouse models, mucosal IgA is associated with protection against challenge and in studies with live attenuated influenza vaccines in man, the presence of mucosal IgA correlates with reduction in virus shedding and resistance to experimental infection. It was concluded that mucosal IgA appears to play a role in protection against influenza virus infection and that more studies should evaluate the ability of vaccines to induce mucosal immune responses . . . ".

Accordingly, the intra-lung delivery route of the present invention is of potential value for vaccines against other infections and provides an alternative route of delivery for vaccines requiring a primarily systemic antibody response.

Furthermore, antigen which is administered in accordance with the present invention induces strong cellular immune responses. Antigen with adjuvant delivered by the intra-lung route stimulates the production of peripheral blood cells which proliferate specifically in response to the antigen. These cells belong to both the CD4+ and CD8+ classes of T cells which have functions in enhancing antibody responses and in carrying out effector functions such as the killing of virus-infected cells. The ability to induce cellular immune responses in addition to antibody responses is of potential value in vaccination against infectious agents, particularly HIV, herpesviruses and bacteria which include an intracellular phase in their lifecycle such as mycobacteria, chlamydia and listeria.

Further features of the present invention are more fully described in the following Examples. It is to be understood, however, that this detailed description is included solely for the purposes of exemplifying the present invention, and should not be understood in any way as a restriction on the broad description of the invention as set out above.

EXAMPLES

Example 1

Background

By way of background to the present invention, the inventors examined modes of vaccine delivery in the cannulated sheep model. Cannulation allows the outflow of the local draining lymph node to be studied in some detail. This work was performed in sheep using ISCOMATRIX™ adjuvant influenza virus vaccine as the vaccine model. A principal finding from this work was that intranasal delivery was highly inefficient, inducing poor local immunity even at high antigen doses.

These findings prompted a change in direction for the project to study the outcome of vaccine delivery in uncannulated sheep by the intra-lung route, by delivering vaccine deep into one lobe of the lung.

Experimental Methods

Blood Collection

Sheep were restrained and 10 mL of blood collected from the jugular vein using a 10 mL syringe and an 18 G needle.

Immunisations

Influenza antigen used in these studies was sucrose gradient purified A/New Calcdonia 20/99 H1N1 virus, which had been inactivated and detergent disrupted (Coulter et al., 1998). Antigen concentration was based on haemagglutinin content and determined by single radial immunodiffusion. GMP grade ISCOMATRIX™ adjuvant was prepared by CSL Limited according to a previously described process (Pearse and Drane, 2005). Prior to immunisation, vaccine formulations were prepared by admixing an appropriate quantity of antigen with ISCOMATRIX™ adjuvant.

For intra-lung immunisations, sheep were carefully restrained in a harness and a bronchoscope inserted via the left nostril to the caudal lobe of the left lung. Vaccine formulations were then infused in a total volume of 5 mL, followed by 10 mL of air to ensure complete delivery.

For subcutaneous immunisations, vaccine formulations were delivered in a total volume of 200 μL in the inner thigh using a 1 mL syringe and a 25 G needle.

Bronchoalveolar Lavage (BAL) Collection

For collection of bronchoalveolar lavage (BAL) samples, a bronchoscope was inserted into restrained sheep as for vaccinations and 10 mL of PBS (phosphate-buffered saline pH7.2) delivered into the lung lobe using a syringe attached to the bronchoscope. The same syringe was then used to withdraw BAL fluid via the bronchoscope.

Evaluation of Antibody Responses by EIA

Anti-influenza antibodies in BAL and serum samples in duplicate were evaluated by EIA (Enzyme Immunoassay). Briefly, 96 well Maxisorp flat bottom plates (NUNC, Roskilde, Denmark) were coated overnight with 50 μL of 10 μg/mL influenza antigen in carbonate buffer, pH9.6. Plates were then blocked with 1% sodium casein before adding 100 μL of 1 in 5 serial dilutions of samples in duplicates. Binding of specific anti-influenza antibodies was detected using rabbit anti-sheep total Ig conjugated with horse radish peroxidase (Dako, Denmark) or anti-bovine/ovine IgA (Serotec, Oxford) followed by rabbit anti-mouse horse radish peroxidase (Dako). Colour was developed by addition of TMB substrate (Zymed, San Francisco), stopped by addition of 2M $H_2SO_4$. Optical density at 450 nm was determined on a Bio-Tek ELx800 plate reader and antibody endpoint titres calculated.

Evaluation of Haemagglutination Inhibition Activity

Serum and BAL samples which gave an antigen-specific antibody response by ELISA were also examined for Haemagglutination Inhibition Activity (HAI). This assay determines the titre of functional antibodies, by measuring the inhibition of red blood cell agglutination by influenza virus. Samples were tested for HAI against egg grown A/New Calcdonia/20/99 virus (H1N1) using turkey red blood cells. The HAI titre was determined as the endpoint dilution that inhibited influenza agglutination of the red blood cells. HAI assays were performed by the WHO Collaborating Centre for Reference and Research on Influenza, Melbourne, Australia.

In Vitro Antigen Restimulation of Peripheral Blood Mononuclear Cells

Blood samples (50 mL) collected from the jugular vein using a syringe and 18 G needle were placed into a 50 mL tube containing 100 μL of 5000 U/mL heparin. The cells were then centrifuged at 800 g for 20 minutes with no brake, the buffy coat collected into a 15 mL tube and diluted to 8 mL with PBS. Using a transfer pipette, 3.5 mL of Ficoll-paque was added to the bottom of the cell suspension, and the samples centrifuged at 1000 g for 30 minutes with no brake. The peripheral blood mononuclear cells were then collected from the Ficoll-PBS interface, washed in PBS and resuspended at $5\times10^6$/mL in complete medium (Dulbecco's Modified Eagles medium supplemented with 10% FCS, L-glutamine, penicillin (100 U/mL), streptomycin (100 μg/mL) and 50 μM 2-mercaptoethanol).

For the antigen restimulation assay, 100 μL of cells ($5\times10^5$/well) were aliquoted into 96-well tissue culture plates, to which were added in triplicate 100 μL of either media alone or media containing 10 or 20 μg/mL A/New Calcdonia influenza antigen (final concentration 5 or 10 μg/mL antigen). After 5 days culture at 37° C. in a humidified incubator, all wells were pulsed with 20 μL of 1 μCi tritiated thymidine for 24 hours. Cells were then harvested onto glass fibre filters using a Packard Harvester, placed into cassettes with Microscint scintillation liquid, and β-radiation measured using an automated microplate scintillation counter.

Evaluation of Immunisation to the Upper and Lower Lung

Examination of the effectiveness of immunisation by delivery to the upper lung, as an alternative to delivery to the lower lung was carried out as described below. FIG. 1 (from Nickel et al., 1979) illustrates the sites of the sheep lung used for delivery to the upper and lower lung.

Vaccine delivered to the 'upper lung'—the vaccine was delivered into the upper lung using a fibre-optic bronchoscope. The vaccine was introduced into the principle bronchi, 1 cm past the major tracheal bifurcation.

Vaccine delivered to the 'lower lung'—the vaccine was delivered deep into the caudal lung using a fibre-optic bronchoscope. The vaccine was introduced where the caudal bronchus joins the caudal segmental bronchi, 10 cm past the major tracheal bifurcation.

Immunisations, bleeds, BAL collection and ELISA assays were carried out as described for the other experiments. The sheep received three doses of 0.04 μg influenza antigen with 100 μg ISCOMATRIX™ adjuvant.

Results

Antibody Induction by Immunisation Via the Intra-Lung Route

In 3 separate experiments sheep were immunised by the intra-lung route. Bleeds were taken at 2 weeks post 1° dose, and one week post 2° and 3° doses Experiment 1 Sheep were immunised with either 1, 5 or 15 μg of antigen plus 100 μg ISCOMATRIX™ adjuvant. Three immunisations were given, 3 weeks apart. Serum samples were collected before commencement, and after each vaccination.

Following the surprising finding that 1 μg of adjuvant influenza antigen delivered intra-lung was as effective as 15 μg, a second experiment examined further reductions in antigen dose.

Experiment 2 Sheep were immunised with either 0.04, 0.2, 1, 5 or 15 μg antigen plus 100 μg ISCOMATRIX™ adjuvant. Three immunisations were given, 3 weeks apart. Serum samples were collected before commencement, and after each immunisation.

These experiments demonstrated that all antigen doses induced significant antibody responses in recipient animals—even as low as 0.04 μg antigen. The lower antigen doses induced very few antibodies after one dose. However, immunity in recipient animals was equivalent to the higher antigen doses following 2 and 3 doses. These antibody responses included functional haemagglutination inhibition (HAI).

Serum IgG and IgA levels in sheep immunised intra-lung with 0.04 μg antigen and 100 μg ISCOMATRIX™ adjuvant were equivalent to those obtained following subcutaneous immunisation with 15 μg of antigen alone (current vaccine dose). The low dose intra-lung immunisations produced very good levels of specific IgA and IgG in the lung (BAL—bronchial alveolar lavage), superior to that induced by the higher doses injected subcutaneously.

Experiment 3 The third experiment evaluated (i) the requirement for adjuvant for inducing significant immunity with low antigen dose, (ii) directly compared low antigen dose (0.04 μg) delivered intra-lung with low dose delivered subcutaneously, (iii) examined even lower antigen doses (0.008 μg antigen).

The third experiment:

(a) repeated the observations made in the first two;
(b) demonstrated that adjuvant was essential for the induction of immunity against very low dose antigen;
(c) found that adjuvanted low dose antigen delivered intra-lung induced similar serum antibodies and superior lung antibodies compared to the same low antigen dose vaccine or the current vaccine dose, delivered subcutaneously;
(d) found that more than 2 doses of adjuvanted very low dose antigen injected subcutaneously appeared to induce a tolerance or inhibitory effect as serum antibodies following a 3rd dose were reduced. This inhibition did not occur following lung delivery;
(e) found that intra-lung immunisation with even 0.008 μg antigen administered with 100 μg ISCOMATRIX™ adjuvant induced significant antibody induction, though less than induced by 0.04 μg antigen with ISCOMATRIX™ adjuvant.

The combined data for experiments 1 to 3 are summarised in FIG. 2 and Table 1.

TABLE 1

Haemagglutination Inhibition (HAI) activity induced by intra-lung immunisation with reducing doses of influenza antigen and ISCOMATRIX ™ adjuvant

| Route | Vaccine | Median HAI titre (Interquartile range) | | | | | |
|---|---|---|---|---|---|---|---|
| | | Serum | | | Bronchoalveolar lavage | | |
| | | Primary | Secondary | Tertiary | Primary | Secondary | Tertiary |
| S/C | 15 μg flu | 5 | 30 | 100 | 0 | 0 | 0 |
| | | (0-18) | (20-100) | (20-440) | (0) | (0) | (0) |
| Lung | 15 μg flu + | 10 | 330 | 60 | 0 | 10* | 10* |
| | IMX | (10) | (20-640) | (35-400) | (0) | (10-20) | (10-20) |
| Lung | 5 μg flu + | 0 | 160 | 240 | 0 | 0 | 40* |
| | IMX | (0) | (120-160) | (70-400) | (0) | (0-10) | (8-50) |
| Lung | 1 μg flu + | 0 | 30 | 160 | 0 | 0 | 5 |
| | IMX | (0) | (15-40) | (140-320) | (0) | (0) | (0-10) |
| Lung | 0.2 μg flu + | 0 | 15 | 160 | 0 | 0 | 5 |
| | IMX | (0) | (0-40) | (65-200) | (0) | (0) | (0-13) |
| Lung | 0.04 μg flu + | 0 | 10 | 160 | 0 | 0 | 30* |
| | IMX | (0) | (0-40) | (140-640) | (0) | (0) | (0-80) |
| Lung | 0.008 μg | 0 | 0 | 20 | 0 | 0 | 0 |
| | flu + IMX | (0) | (0) | (0-40) | (0) | (0) | (0) |

Table 1 legend:

Data is combined from 3 separate experiments. Groups of sheep (n = 8 per group, except the 15 μg flu group (n = 12) and the 0.04 μg flu + IMX group (n = 16)) were immunised in the left lung with reducing doses of split virion influenza antigen plus 100 μg of ISCOMATRIX ™ adjuvant (IMX). A group of vaccine control sheep were immunised subcutaneously (S/C) with an equivalent dose of one strain of the current human influenza vaccine (15 μg influenza antigen alone). Sheep received 3 immunisations, spaced by 3 weeks. Sera and left lung washings (BAL) were collected from all sheep one week prior to and two weeks after the primary dose and one week after the secondary and tertiary doses. The titration of these samples which inhibited influenza mediated haemagglutination was then determined. All preimmunisation samples were negative for HAI activity (not shown).

*Significantly higher HAI titre compared with subcutaneously immunised control (Mann Whitney; $p < 0.004$).

The data for experiment 3 are shown in Table 2 and FIG. 3.

TABLE 2

Requirement of adjuvant and route of delivery on Haemagglutination Inhibition activity induced by immunisation with extremely low doses of influenza antigen

| Route | Vaccine | Median HAI titre (Interquartile range) | | | | | |
|---|---|---|---|---|---|---|---|
| | | Serum | | | Bronchoalveolar lavage | | |
| | | Primary | Secondary | Tertiary | Primary | Secondary | Tertiary |
| S/C | 15 μg flu | 0 | 30 | 30 | 0 | 0 | 0 |
| | | (0-3) | (20-100) | (18-160) | (0) | (0) | (0) |
| S/C | 0.04 μg | 0 | 10 | 25 | 0 | 0 | 0 |
| | flu | (0) | (0-40) | (8-50) | (0) | (0) | (0) |
| S/C | 0.04 μg | 20*^ | 320*^ | 160^ | 0 | 0 | 0 |
| | flu + IMX | (8-20) | (280-400) | (80-320) | (0) | (0) | (0) |
| Lung | 0.04 μg | 0 | 0# | 0# | 0 | 0 | 0 |
| | flu | (0) | (0) | (0) | (0) | (0) | (0) |
| Lung | 0.04 μg | 0 | 5 | 160^ | 0 | 0 | 60*^ |
| | flu + IMX | (0) | (0-18) | (80-200) | (0) | (0) | (30-100) |

Table 2 legend:

Groups of sheep (n = 8) were immunised in the left lung with an extremely low dose (0.04 μg) of split virion influenza antigen with or without 100 μg of ISCOMATRIX ™ adjuvant (IMX). Other groups received the same vaccines injected subcutaneously (S/C). One group of control sheep was immunised subcutaneously with an equivalent antigen dose of one strain of the current human influenza vaccine (15 μg influenza antigen alone). Sheep received 3 immunisations, spaced by 3 weeks. Sera and left lung washings (BAL) were collected from all sheep one week prior to and two weeks after the primary immunisation and one week after the secondary and tertiary doses. The titration of these samples which inhibited influenza mediated haemagglutination was then determined. All preimmunisation samples were negative for HAI activity (not shown).

#Significantly lower HAI titre compared with subcutaneously immunised control (Mann Whitney; $p < 0.002$).

*Significantly higher HAI titre compared with subcutaneously immunised control (Mann Whitney; $p < 0.028$).

^Significantly higher HAI titre compared with unadjuvanted group (Mann Whitney; $p < 0.01$).

In FIGS. 1 and 2:

Horizontal bar=median value

Open bar=middle 50% of values

Vertical line=10 and 90 percentiles.

IMX=ISCOMATRIX™ adjuvant

The bars show the influenza-specific endpoint antibody titre after the first ($1^0$), second ($2^0$) and third ($3^0$) immunisations as described above.

In FIG. 1: *Significantly greater than 15 μg s/c group (Mann-Whitney; p<03).

In FIG. 2

Significantly less than 15 µg s/c group (Mann-Whitney; p<0.01).

* Significantly greater than 15 µg s/c group (Mann-Whitney; p<0.038).

^ Significantly greater than unadjuvanted vaccine delivered via the same route (Mann-Whitney; p<0.038).

§Subcutaneous, significantly greater than same vaccine delivered intralung (Mann-Whitney; p<0.028).

✓ℭ Intralung, significantly greater than same vaccine delivered subcutaneously (Mann-Whitney; p<0.021).

Experiment 4 This experiment evaluated the effectiveness of delivery of adjuvanted influenza antigen to the upper lung, in comparison with delivery to the lower lung used in earlier experiments. Two groups of 8 sheep received a formulation containing 0.04 µg influenza antigen and 100 µg ISCOMATRIX™ adjuvant to either the upper or lower lung three times and serum and BAL antibody responses were examined by EIA (FIG. 4).

These results indicated that after three doses, although delivery to the upper lung induced serum and BAL responses, significantly better responses in both serum and BAL for both IgG and IgA were induced by lower lung delivery.

Summary

Intra-lung immunisation with influenza virus antigen with 100 µg ISCOMATRIX™ adjuvant proved highly efficient in the induction of both systemic and mucosal (BAL) antibody responses with HAI activity.

Strong serum antibody responses were observed even at extremely low levels of antigen (0.04 µg influenza antigen with ISCOMATRIX™ adjuvant). These responses were much stronger than those induced by subcutaneous injection (s/c) of 15 µg of influenza antigen alone (as per the current vaccine) and matched those induced by subcutaneous 0.04 µg influenza antigen with ISCOMATRIX™ adjuvant.

The mucosal antibody response induced by intra-lung delivery of 0.04 µg influenza antigen with ISCOMATRIX™ adjuvant was greatly elevated compared with subcutaneous 15 µg of influenza antigen or subcutaneous 0.04 µg influenza antigen with ISCOMATRIX™ adjuvant. Neither of the latter induced detectable mucosal (lung) responses.

Example 2

Cellular Immunity Induction by Vaccination Via the Intra-Lung Route

Sheep received 4 intra-lung immunisations with either 0.04 µg influenza antigen alone, or 0.04 µg influenza+100 µg ISCOMATRIX™ adjuvant. One week after the last immunisation, peripheral blood was collected, and mononuclear cells cultured in 96 well plates with either media alone (negative control), or 5 or 10 µg influenza antigen (restimulated). After five days, wells were pulsed with tritiated thymidine for 24 hours. Radioactivity was then measured to enumerate cell proliferation. The Stimulation Indices were calculated by dividing the mean counts per minute (cpm) for the restimulated group by the mean cpm for the medium alone control group.

The results of a cell proliferation study are shown in Table 3. When sheep were vaccinated intra-lung with antigen alone, no proliferative response was detectable in the peripheral blood. However, such a response was detected in sheep which received antigen with ISCOMATRIX™ adjuvant. These data demonstrate the requirement for adjuvant, following lung vaccine delivery, to induce a cellular proliferative memory response in the peripheral circulation.

TABLE 3

Proliferative response of influenza-stimulated peripheral blood mononuclear cells, from sheep immunised intra-lung with low dose antigen, with or without ISCOMATRIX ™ adjuvant

| Intra-lung vaccination | | Median Stimulation Index (Interquartile Range) following restimulation with | |
|---|---|---|---|
| | | 5 µg influenza | 10 µg influenza |
| Vaccine | Group size | antigen | antigen |
| 0.04 µg influenza | n = 8 | 1 (1-2) | 1 (1-3) |
| 0.04 µg influenza + 100 µg ISCOMATRIX ™ adjuvant | n = 8 | 6 (2-16) | 10 (3-25) |

Example 3

Formulation of Antigen with Microfluidised Oil-in-Water Adjuvant for Administration by the Intra-Lung Route Antigen at an appropriate concentration (to result in a final antigen concentration yielding a single dose in the range 0.01 to 500 µg) is mixed with 5% v/v Squalane, 0.5% v/v Tween 80, 0.5% v/v Span 85 in PBS pH 7.2, 0.05% sodium azide. This mixture is then subjected to high pressure microfluidisation at a pressure of 19-20,000 pounds per square inch (psi). The microfluidisation is repeated a further seven times. The formulation is delivered via the intra-lung route by the methods described above.

Example 4

Systemic and Mucosal Immunity Induced by Immunisation Via the Intra-Lung Route with Recombinant Cytomegalovirus gB Antigen Formulated with ISCOMATRIX™ Adjuvant In order to confirm and extend observations made with influenza antigen and ISCOMATRIX™ adjuvant, studies were performed in sheep examining the immune responses induced by intra-lung delivery of a recombinant viral antigen. A truncated form of cytomegalovirus gB glycoprotein (CMV gB) formulated with ISCOMATRIX™ adjuvant was delivered by the intra-lung and subcutaneous routes and antibody responses in serum and lung assessed by EIA. In addition, induction of functional antibodies was assessed by assay of CMV-neutralising antibodies in serum. The ability of formulations delivered intra-lung to induce T cell responses was also examined by assessing gB-specific cell proliferation of peripheral blood mononuclear cells Experimental Methods Production of Truncated Recombinant Human CMV gB Protein (ΔgB)

1. Generation of Plasmid Containing DNA Encoding ΔgB Protein.

DNA encoding a truncated form of CMV gB which had been engineered to remove the transmembrane region of the protein was provided by Assoc. Prof. Rajiv Khanna, Queensland Institute of Medical Research, Brisbane, Australia. This DNA encoded a protein containing the signal sequence of Tissue Plasminogen Activator (TPA) with the ecto- and cytoplasmic domains (NCBI P06473) of gB fused in frame. As well, the DNA was point mutated at the nucleotides encoding the region around amino acids 460/461 to prevent cleavage of the expressed protein. The DNA was cloned into the pCEP4 vector (Invitrogen) as a KpnI/NotI fragment. The resulting plasmid (pCEP4ΔgB) was amplified in *E. coli* and purified plasmid prepared using Qiagen Maxi Kit.

2. Expression of ΔgB Protein in Mammalian Cells

Cultures of FreeStyle™ 293-F cells grown in FreeStyle™ Expression Medium (Invitrogen) in shake flasks at 37° C. were transfected with pCEP4ΔgB using 293fectin transfection reagent (Invitrogen). Secreted expression of the protein ΔgB under selection using Hygromycin B in the cultures was determined by SDS-PAGE gel analysis of cell supernatant samples. Cell culture supernatants were harvested and clarified by centrifugation at 2500 rpm and then passed through a 0.45 μm filter prior to chromatography.

3. Purification of ΔgB Protein

The ΔgB protein was purified using affinity chromatography by capture with the gB-specific monoclonal antibody 58-15 (Singh and Compton, 2000). The antibody was purified on a Prosep-A (Millipore) protein A column. For purification of ΔgB protein, the purified antibody was coupled to a HiTrap NHS-activated HP column (Pharmacia-Amersham) in equilibration buffer (0.2M $NaHCO_3$/0.5M NaCl, pH8.3). Clarified cell culture supernatant was diluted 1:1 with 100 mM Borate/150 mM NaCl pH8.5. The diluted supernatant was applied to the HiTrap column, equilibrated with equilibration buffer and eluted firstly with 0.1M Glycine-HCl pH2.5, followed by equilibration buffer and eluted again, this time with 0.15M Ammonium Hydroxide pH10.5. Eluted fractions were neutralised using either 3M Tris pH8 or 1M Glycine pH2.5. Protein purity was examined by Coomassie-stained SDS-PAGE gel electrophoresis (FIG. 5). Protein concentration was estimated by determining the OD at 280 nm.

Immunisation of Sheep with ΔgB

Blood Collection

Methods were the same as those described in Example 1.

Immunisations

Groups of sheep were immunised with ΔgB protein formulated with ISCOMATRIX™ adjuvant Table 4). ΔgB protein from cytomegalovirus was prepared as described.

All sheep received three vaccine doses, the details of which, including the blood collection schedule are described in Example 1.

TABLE 4

Groups of sheep were immunised by the indicated route with ΔgB protein formulated with ISCOMATRIX ™ adjuvant.

| Group | Size | Route of delivery | Antigen | Adjuvant |
|---|---|---|---|---|
| 1 | n = 8 | Subcutaneous | 15 μg CMV ΔgB | 100 μg ISCOMATRIX ™ adjuvant |
| 2 | n = 8 | Intra-lung | 15 μg CMV ΔgB | ISCOMATRIX ™ adjuvant |

BAL Collection

Collection of BAL samples was performed as described in Example 1.

Evaluation of Antibody Responses by EIA

Methods for detecting sheep IgG and IgA were similar to those in Example 1 with the following exceptions. Plates (96 well) were coated overnight with 100 μl per well of 2 μg/mL purified ΔgB protein in PBS. Bound sheep IgG was detected with rabbit anti-sheep IgG (H+L) conjugated to horse radish peroxidise (Southern Biotech). In the case of both IgG and IgA TMB peroxidise substrate was sourced from KPL Kirkegaard and Perry Laboratories respectively. The reaction was stopped by addition of 50 μl per well 0.5M $H_2SO_4$.

Evaluation of Functional Activity Against CMV

The capacity of the vaccines to induce functional serum antibodies was assessed using a neutralisation assay based on recombinant human cytomegalovirus infection of MRC-5 cells. Assays were performed by Assoc. Prof. Rajiv Khanna and colleagues, Queensland Institute of Medical Research, Brisbane, Australia, using recombinant CMV Ad169 wt86-EGFP expressing green fluorescent protein (Marschall et al., 2000; Wang et al., 2004). After exposure of Ad169wt86-EGFP to serum dilutions, the ability of the virus to infect human fibroblasts (MRC-5 cells) was assessed by quantifying the percentage cell nuclei fluorescing using flow cytometry (FACS). The procedure is described below:

1. Sera from the sheep were incubated at 56° C. for 30 minutes.
2. Sera from the sheep (neat and at 2-fold and 4-fold dilutions in 10041 DMEM) were dispensed in a 96 well tray.
3. 25 μl ($2.5\times10^4$ PFU) Ad169wt86-EGFP virus was added to each serum sample.
4. Serum/virus samples were incubated at 37° C. for 2 hours in 7% $CO_2$ in air.
5. Previously, 48 well flat-bottom trays containing MRC-5 cells, grown on DMEM with 10% foetal bovine serum (DMEM-10) by incubation at 37° C. in 7% $CO_2$ in air, had been prepared and were at 80-90% confluency at time of use.
6. The cell culture medium was removed from the MRC-5 cells. 50 μl of each virus/serum sample was then transferred to corresponding wells in the 48 well flat-bottom trays containing MRC-5 cells, 50 μl DMEM added and the 48 well trays incubated at 37° C. for 2 hours in 7% $CO_2$ in air with gentle rocking.
7. The inoculum was aspirated from the 48 well trays, the wells washed three times with DMEM-10, and then 500 μl DMEM-10 added to each well, and incubated at 37° C. in 7% $CO_2$ in air overnight.
8. The next day the cell medium and cells (using trypsin) were harvested from the 48 well trays and the cells pelleted by centrifugation.
9. The pellets were resuspended in PBS and pelleted again by centrifugation.
10. The pellets were resuspended vigorously in 100 μl of hypotonic buffer (0.1% sodium citrate, 0.1% (v/v) Triton X-100) containing 0.2 μl mg/mL 7-Aminoctinmycin D and left for 20 minutes at room temperature in the dark.
11. Samples of each pellet were transferred to tubes suitable for FACS analysis and PBS containing 1% Paraformaldehyde added. The mixture was left on ice for 30 minutes prior to FACS analysis.
12. The samples were analysed on a Becton Dickinson FACSCanto and the percentage of fluorescing nuclei in the samples quantified.
13. The percentage neutralisation for each sample was calculated using the formula:

% neutralisation=[percentage of fluorescing nuclei (no serum added)−percentage of fluorescing nuclei (serum sample)−percentage of fluorescing nuclei (no serum added)]×100.

In Vitro Antigen Restimulation of Peripheral Blood Mononuclear Cells

Blood samples (50 mL) collected from the jugular vein using a syringe and 18 G needle were placed into a 50 mL tube containing 100 μL of 5000 U/mL heparin. The cells were then centrifuged at 800 g for 20 minutes with no brake, the buffy coat collected into a 15 mL tube and diluted to 8 mL with PBS. Using a transfer pipette, 3.5 mL of Ficoll-paque was added to the bottom of the cell suspension, and the samples centrifuged at 1000 g for 30 minutes with no brake. The peripheral blood mononuclear cells were then collected from the Ficoll-PBS interface, washed in PBS and resuspended at $5\times10^6$/mL in complete medium (Dulbecco's Modified Eagles medium supplemented with 10% FCS, L-glutamine, penicillin (100 U/mL), streptomycin (100 μg/mL) and 50 μM 2-mercaptoethanol).

For the antigen restimulation assay, 100 μL of cells ($5\times10^5$/well) were aliquoted into 96-well tissue culture plates, to which were added in triplicate 100 μL of either media alone or media containing 5, 10, 20 or 40 μg/mL gB protein (final concentration 2.5, 5, 10 or 20 μg/mL). After 5 days culture at 37° C. in a humidified incubator, all wells were pulsed with 20 μL of 1 μCi tritiated thymidine for 24 hours. Cells were then harvested onto glass fibre filters using a Packard Harvester, placed into cassettes with Microscint scintillation liquid, and β-radiation measured using an automated microplate scintillation counter.

Results

Immune Responses Following Intra-Lung and Subcutaneous Immunisation with Recombinant CMV ΔgB Antigen Formulated with ISCOMATRIX™ Adjuvant Sheep received three subcutaneous or intra-lung doses, at 3 week intervals of the CMV ΔgB antigen formulated with ISCOMATRIX™ adjuvant. Sera and BAL samples were collected one week prior to the first dose, 2 weeks after the first dose and 1 week after the second and third doses. For antibody EIA data, preimmunisation antibody titres were subtracted.

The results of these experiments with ΔgB formulated with ISCOMATRIX™ adjuvant (FIG. 6) were broadly similar to those shown in Example 2 using low dose influenza antigen (0.04 μg) formulated with ISCOMATRIX™ adjuvant, where serum IgG and IgA responses following intra-lung were equivalent to those for subcutaneous delivery after three doses. However, in contrast to the results obtained with influenza antigen formulations, ΔgB formulated with ISCOMATRIX™ adjuvant delivered by the intra-lung route induced equivalent serum IgG and IgA to subcutaneous delivery after only two doses and a significantly higher serum IgG when responses after one dose were examined (FIGS. 6*a* and *b*).

In the case of antibody responses in the lung, responses following immunisation with ΔgB formulated with ISCOMATRIX™ adjuvant again paralleled observations made with low dose influenza antigen formulated with ISCOMATRIX™ adjuvant. ΔgB formulated with ISCOMATRIX™ adjuvant induced significantly higher antibody responses in the lung after three doses when delivered intra-lung when compared to subcutaneous delivery of the same formulation (FIGS. 6*c* and *d*).

In the case of functional antibody induction, the results for the CMV neutralisation assays on sera were in agreement with those obtained in the EIA for serum IgG responses (FIG. 7). Neutralising antibody responses induced by both intra-lung and subcutaneous delivery of ΔgB formulated with ISCOMATRIX™ adjuvant were significantly higher than in the preimmunisation sera. The neutralising responses increased further after three doses. The results indicate equivalence in induction of neutralising antibodies in serum when antigen formulated with ISCOMATRIX™ adjuvant was delivered by the intra-lung and subcutaneous routes.

The results from assay of restimulation of peripheral blood mononuclear cells with ΔgB (FIG. 8), indicate that antigen formulated with ISCOMATRIX™ adjuvant delivered by either the intra-lung or subcutaneous routes induced T cell responses after two to three doses (stimulation index of 4 or greater). The two routes of delivery induced equivalent T cell responses.

Example 5

Systemic and Mucosal Immunity Induced by Vaccination Via the Intra-Lung Route with Different Adjuvant Technologies These studies were performed to examine whether adjuvants other than ISCOMATRIX™ adjuvant were able to induce antigen-specific mucosal and systemic antibody responses when delivered by the intra-lung route. Groups of sheep were immunised intra-lung with influenza antigen formulated with several alternative adjuvants and the responses compared with an ISCOMATRIX™ adjuvant formulation (Table 5).

TABLE 5

Groups of sheep immunised by the intra-lung route with influenza antigen formulated with various adjuvant formulations

| Group | Size | Influenza antigen dose (μg) | Adjuvant |
|---|---|---|---|
| 1 | n = 4 | 15 | — |
| 2 | n = 7 | 15 | 100 μg ISCOMATRIX ™ adjuvant |
| 3 | n = 7 | 15 | 100 μg ISCOMATRIX ™ adjuvant + 50 μg MPL |
| 4 | n = 7 | 15 | 1 mg liposomes + 50 μg MPL |
| 5 | n = 7 | 15 | 1 mg liposomes + 750 μg CpG |

Experimental Methods

Preparation of Adjuvant Formulations

A. Liposomes were Prepared by the Following Method:

Buffer Solutions:

IR buffer: 0.14M NaCl, 3 mM KCl, 8 mM $Na_2HPO_4$, 0.05 mM $CaCl_2.2H_2O$, 1.5 mM $KH_2PO_4$ pH7.2

IVD buffer: 0.14M NaCl, 3.5 mM $Na_2HPO_4$, 1.4 mM $NaH_2PO_4.2H_2O$ pH7.2

1. A solution of 11.4 mg/mL cholesterol, 12.4 mg/mL dipalmitoylphosphatidylcholine (DPPC) and Mega10 was prepared in IR buffer (Chol/DPPC).
2. Chol/DPPC was diluted 1/40 gradually over 30 minutes by addition of IVD buffer.
3. The diluted solution was concentrated by ultrafiltration at 40° C. using an ST 200 Diafiltration Cartridge (Nephral) to 1/40 of the original diluted volume.
4. The concentrated solution was washed by ultrafiltration with 25 volumes of IVD buffer.
5. The Chol/DPPC solution was concentrated 2 fold by further ultrafiltration.
6. Prior to lipid extrusion Chol/DPPC was incubated at 40° C. for at least 1 hour.
7. Liposomes were extruded from Chol/DPPC using a lipid extruder (T.001 Northern Lipids Inc., Canada) fitted with a 10 mL Thermobarrel Extruder maintained at 42° C. throughout the procedure.

8. Extrusion was carried out on 10 mL lots of Chol/DPPC using a pressure of 1400-2000 kPa through a 0.1 μm PC disc filter.
9. The process was repeated until all of the Chol/DPPC solution had been subjected to 10 passes through the system.
10. The resulting liposomes were assayed for cholesterol and DPPC content and examined under the electron microscope using negative staining to assess size and homogeneity.

B. Preparation of MPL

Lipid A monophosphoryl (MPL) (Sigma L6895) was resuspended in DMSO (Sigma D2650) at 2 mg/mL and maintained at 4° C. until use.

C. Preparation of CpG

CpG (Sigma-Genosys 1062 4856-011) was resuspended in 10 mM Tris/1 mM EDTA pH8 and maintained at 4° C. until use.

D. Preparation of Adjuvant Formulations

All adjuvant formulations were prepared by mixing the relevant components using PBS as diluent prior to the addition of Influenza antigen (Table 5). Following this, the formulations containing liposomes were subjected to sonication in a VirSonic sonicator at setting 4 using a ⅛ inch probe. The formulations received two 5 second sonications separated by 30 seconds, all performed on ice.

Immunisations

Groups of sheep were immunised with the influenza antigen and adjuvant formulations described in Table 5, and bleeds taken, using the methods described in Example 1.

BAL Collection

Collection of BAL samples was performed as described in Example 1.

Evaluation of Antibody Responses by ELISA

Assay of antibody responses to influenza antigen in serum and BAL samples was performed as described in Example 1.

Evaluation of Haemagglutination Inhibition Activity

Assay of HAI activity in serum and BAL samples was performed as described in Example 1.

Results

Evaluation of Immune Responses Following Intra-Lung Vaccination with Formulations of Influenza Antigen with a Variety of Adjuvants.

Sheep received three doses at 3 week intervals. Sera and lung (BAL) samples were collected prior to and 2 weeks after the first dose, and 1 week after the second and third doses. For antibody ELISA data, pre-immunisation antibody titres were subtracted.

The results of these experiments demonstrated that different adjuvant formulations varied in their ability to induce antibody responses when combined with antigen and delivered by the intra-lung route (FIGS. 9 and 10).

All adjuvants conferred some benefit in comparison with antigen alone in the induction of antibody in serum. Formulations containing ISCOMATRIX™ adjuvant induced significantly better responses than antigen alone after three doses in both serum and BAL and in the case of serum IgG induced superior responses after two doses. Of particular note is the data showing induction of functional (HAI) antibodies by both ISCOMATRIX™adjuvant formulations in serum after two doses and in BAL after three doses (FIG. 10).

The data (FIG. 9) also suggests an effect from the addition of MPL to ISCOMATRIX™ adjuvant formulations, in that significant increases over adjuvant alone in serum IgG and IgA antibodies occurred after one and two doses respectively, in sheep immunised with the formulation containing antigen and ISCOMATRIX™ adjuvant plus MPL.

REFERENCES

Casetti, M. C., et al. Report of a consultation on role of immunological assays to evaluate efficacy of influenza vaccines. Initiative for Vaccine Research and Global Influenza Programme, World Health Organization, Geneva, Switzerland, 25 Jan. 2005. *Vaccine* (2006), 24(5):541-543.

Coulter, A. et al. Studies on experimental adjuvanted influenza vaccines: comparison of immune stimulating complexes (Iscoms™) and oil-in-water vaccines. *Vaccine* (1998), 16 (11/12): 1243-1253.

Cox, J. C. and Coulter, A. R. Adjuvants—a classification and review of their modes of action. *Vaccine* (1997), 15(3):248-256.

Edwards, D. A. and Dunbar, C. Bioengineering of therapeutic aerosols. *Annu Rev Biomed Eng* (2002), 4:93-107.

Gonda, I. The ascent of pulmonary drug delivery. *J Pharm Sci* (2000), 89:940-5

Griffith, G. D., et al. Liposomally-encapsulated ricin toxoid vaccine delivered intratracheally elicits a good immune response and protects against a lethal pulmonary dose of ricin toxin. *Vaccine* (1997), 15 (17/18): 1933-1939.

Kuo, M. and Lechuga-Bellesteros, D. U.S. Pat. No. 6,518, 239.

Marschall, M., et al. Recombinant green fluorescent protein-expressing human cytomegalovirus as a tool for screening antiviral agents. *Antimicrobial Agents and Chemotherapy* (2000), 44 (6): 1588-1597.

Nickel, R., Schummer A. and Seiferle E. Eds. The Viscera of the Domestic Animals. 2nd edition. Verlag Paul Parey, Berlin (1979).

Pearse, M. J. and Drane, D. ISCOMATRIX™ adjuvant for antigen delivery. Adv. Drug. Del. Rev. (2005), 57:465-474.

Oya Alpa, H., et al. Biodegradeable mucoadhesive particulates for nasal and pulmonary antigen and DNA delivery. *Advanced Drug Delivery Reviews* (2005), 57:411-430.

Shoyele, S. A. and Slovey, A. Prospects for formulating proteins/peptides as aerosols for pulmonary drug delivery. *International Journal of Pharmaceutics* (2006), 314:1-8.

Singh J. and Compton T. Characterisation of a panel of insertion mutants in human cytomegalovirus glycoprotein B. *Journal of Virology* (2000) 74: 1383-1392.

Wang, Z., et al Development of an efficient fluorescence-based microneutralisation assay using recombinant human cytomegalovirus strains expressing green fluorescent protein. *Journal of Virological Methods* (2004), 120: 207-215.

The invention claimed is:

1. A method for eliciting or inducing an immune response in a human or animal subject, which comprises administering to said subject by an intra-lung route a composition comprising:

as the only antigen component, an antigen selected from the group consisting of protein antigens, peptide antigens, and polypeptide antigens, and, as the only adjuvant component(s), one or more adjuvants selected from the group consisting of saponin-based adjuvants, aluminium salt adjuvants, lipopolysaccharide adjuvants. and oligonucleotide adjuvants.

2. The method of claim 1, wherein the composition is formulated for intra-lung administration.

3. The method of claim 2, wherein the composition is an aerosol or in dry powder form.

4. The method of claim 1, wherein the composition is delivered to the subject by oral inhalation.

5. The method of claim 1, wherein the composition is delivered to the lower lung of the subject.

6. The method of claim 1, wherein the one or more adjuvants comprises an immunostimulating adjuvant.

7. The method of claim 6, wherein the one or more adjuvants comprises an immunostimulating complex.

8. The method of claim 7, wherein the one or more adjuvants comprises an immunostimulating molecule comprising a saponin, cholesterol and phospholipid.

9. The method of claim 6, wherein the one or more adjuvants comprises an immunostimulating complex in combination with another immunostimulating adjuvant.

10. The method of claim 9, wherein the one or more adjuvants comprises an immunostimulating complex in combination with a lipopolysaccharide adjuvant.

11. The method of claim 10, wherein the one or more adjuvants comprises an immunostimulating molecule comprising a saponin, cholesterol and phospholipid in combination with monophosphoryl lipid A (MPL).

12. The method of claim 1, wherein the antigen is an antigen which elicits or induces an immune response against a lung pathogen.

13. The method of claim 12, wherein the lung pathogen is influenza virus, *Chlamydia pneumoniae* respiratory syncytial virus or pneumococci.

14. The method of claim 1, wherein the antigen is an antigen which elicits or induces an immune response against a pathogen of non-lung mucosal sites.

15. The method of claim 14, in which the pathogen is *Helicobacter pylori; Salmonella E. coli*, cholera, HIV, or a sexually transmitted disease organism.

16. The method of claim 1, wherein the antigen is a tumour specific or tumour associated antigen.

17. The method of claim 16, wherein the tumour is associated with a mucosal site.

18. The method of claim 17, wherein the tumour is a lung tumour, a tumour of the gastrointestinal tract, or a genital tract tumour.

19. The method of claim 1, wherein the adjuvant is a saponin-based adjuvant.

* * * * *

UNITED STATES PATENT AND TRADEMARK OFFICE

CERTIFICATE OF CORRECTION

PATENT NO. : 9,150,619 B2
APPLICATION NO. : 12/439054
DATED : October 6, 2015
INVENTOR(S) : Stirling John Edwards et al.

It is certified that error appears in the above-identified patent and that said Letters Patent is hereby corrected as shown below:

On the Title Page, item (54) and in the Specification, column 1, lines 1 and 2, please replace "METHOD OF ELICTING OR INDUCING AN IMMUNE RESPONSE" with -- METHOD OF ELICITING OR INDUCING AN IMMUNE RESPONSE --.

Signed and Sealed this
Twenty-ninth Day of March, 2016

Michelle K. Lee

Michelle K. Lee
*Director of the United States Patent and Trademark Office*